(12) United States Patent
Motamedi et al.

(10) Patent No.: US 7,863,038 B2
(45) Date of Patent: Jan. 4, 2011

(54) IMPLANTABLE BIOSENSOR FROM STRATIFIED NANOSTRUCTURED MEMBRANES

(75) Inventors: Massoud Motamedi, Houston, TX (US); Nicholas A. Kotov, Stillwater, OK (US); James P. Wicksted, Stillwater, OK (US); Rinat Esenaliev, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 416 days.

(21) Appl. No.: 10/403,845

(22) Filed: Mar. 31, 2003

(65) Prior Publication Data

US 2004/0023317 A1 Feb. 5, 2004

Related U.S. Application Data

(60) Provisional application No. 60/368,921, filed on Mar. 29, 2002.

(51) Int. Cl.
*C12M 1/36* (2006.01)
(52) U.S. Cl. .............. 435/287.8; 435/287.7; 435/288.7; 436/518; 436/528; 427/2.11; 427/2.13; 427/2.22
(58) Field of Classification Search .................. 424/9.1, 424/9.6, 9.8, 422, 423; 436/14; 123/635
See application file for complete search history.

(56) References Cited

U.S. PATENT DOCUMENTS

| | | | | |
|---|---|---|---|---|
| 4,703,756 A | * | 11/1987 | Gough et al. | 600/347 |
| 5,628,310 A | * | 5/1997 | Rao et al. | 600/317 |
| 6,051,437 A | * | 4/2000 | Luo et al. | 436/172 |
| 6,480,282 B1 | * | 11/2002 | Chinowsky et al. | 356/445 |
| 6,485,703 B1 | * | 11/2002 | Cote et al. | 424/9.1 |
| 6,673,596 B1 | * | 1/2004 | Sayler et al. | 435/288.7 |
| 2001/0046518 A1 | * | 11/2001 | Sawhney | 424/486 |
| 2002/0137058 A1 | * | 9/2002 | Mirkin et al. | 435/6 |
| 2003/0124332 A1 | * | 7/2003 | Mao et al. | 428/304.4 |
| 2003/0152703 A1 | * | 8/2003 | Hammond et al. | 427/256 |
| 2003/0157260 A1 | * | 8/2003 | Rubner et al. | 427/402 |

\* cited by examiner

*Primary Examiner*—N. C. Yang
(74) *Attorney, Agent, or Firm*—Robert W Strozier

(57) ABSTRACT

A new class of biosensors and methods for making and using same are disclosed. The biosensors are multi-layered membrane composites, where at least one layer is prepared by the layer-by-layer process and at least one layer is responsive to changes is a property of a biological system such as changes in the concentration of an atom, ion, molecule or molecular assembly. Because the biosensors are multi-layered, a single biosensor is capable monitor a number of different properties of a biological system simultaneously. The biosensors are monitored by systems that impinge an excitation waveform on the biosensors and analyze a reflected and/or a transmitted resultant waveform. Additionally, the biosensors can be associated with field activated electronic components so that implantable, self-contained analytical devices can be constructed and monitored by field generators, where data is transmitted to an analyzer after field activation.

46 Claims, 19 Drawing Sheets

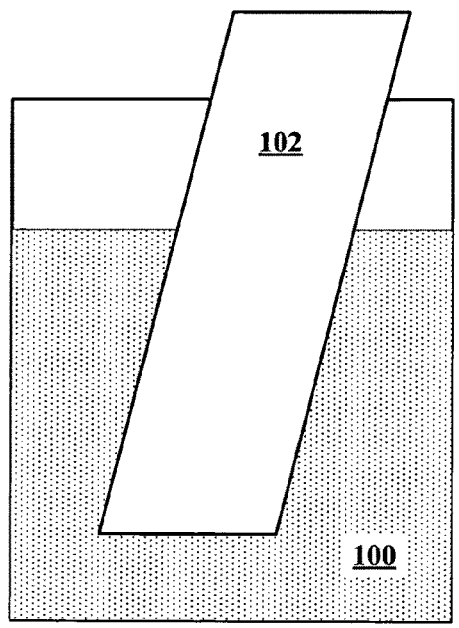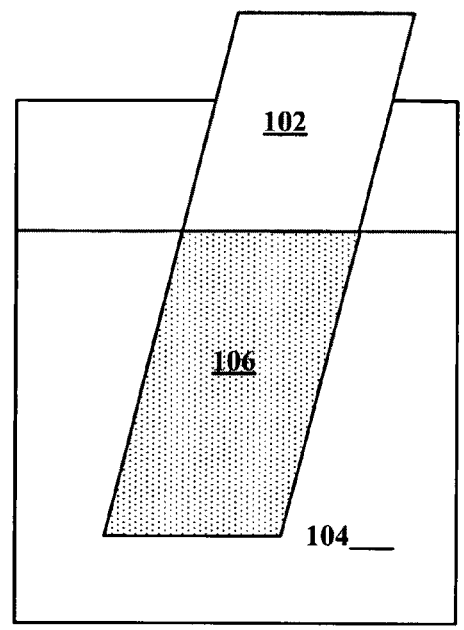
FIG. 1A     FIG. 1B
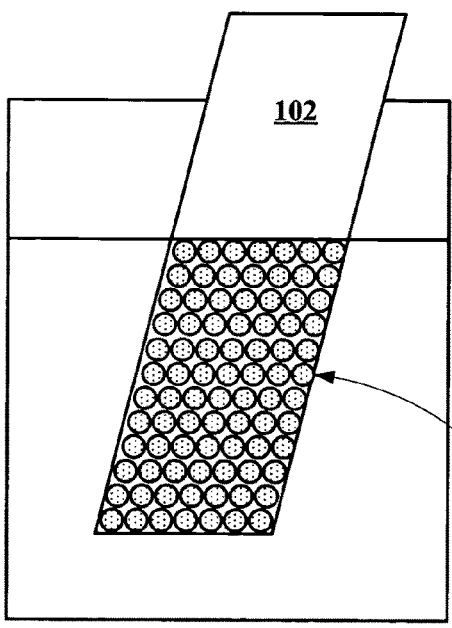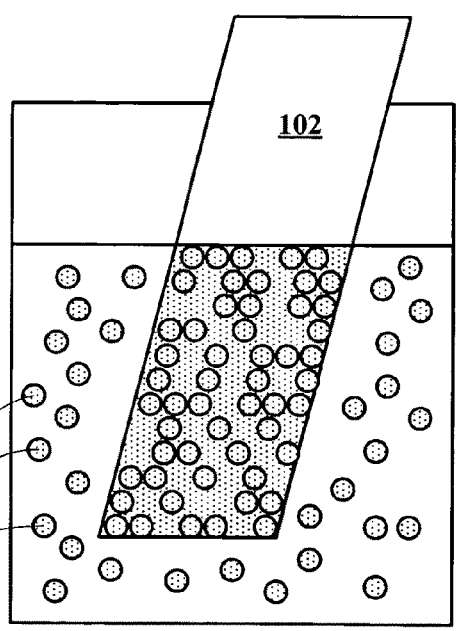
FIG. 1C     FIG. 1D

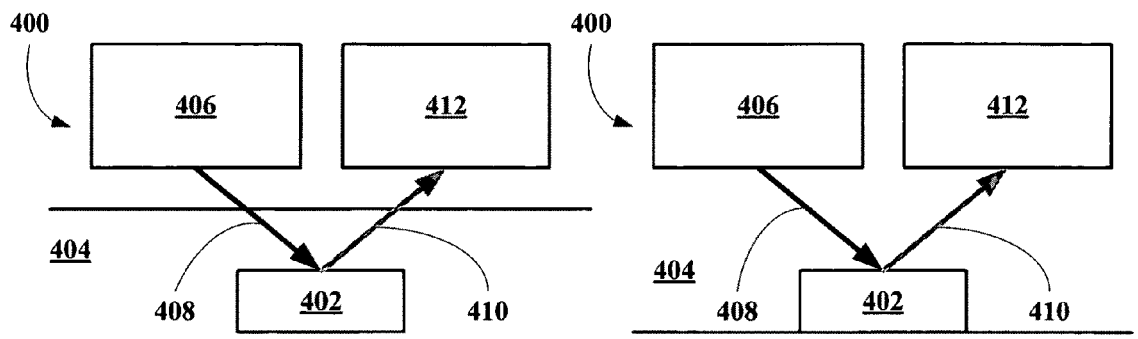
FIG. 4A        FIG. 4B
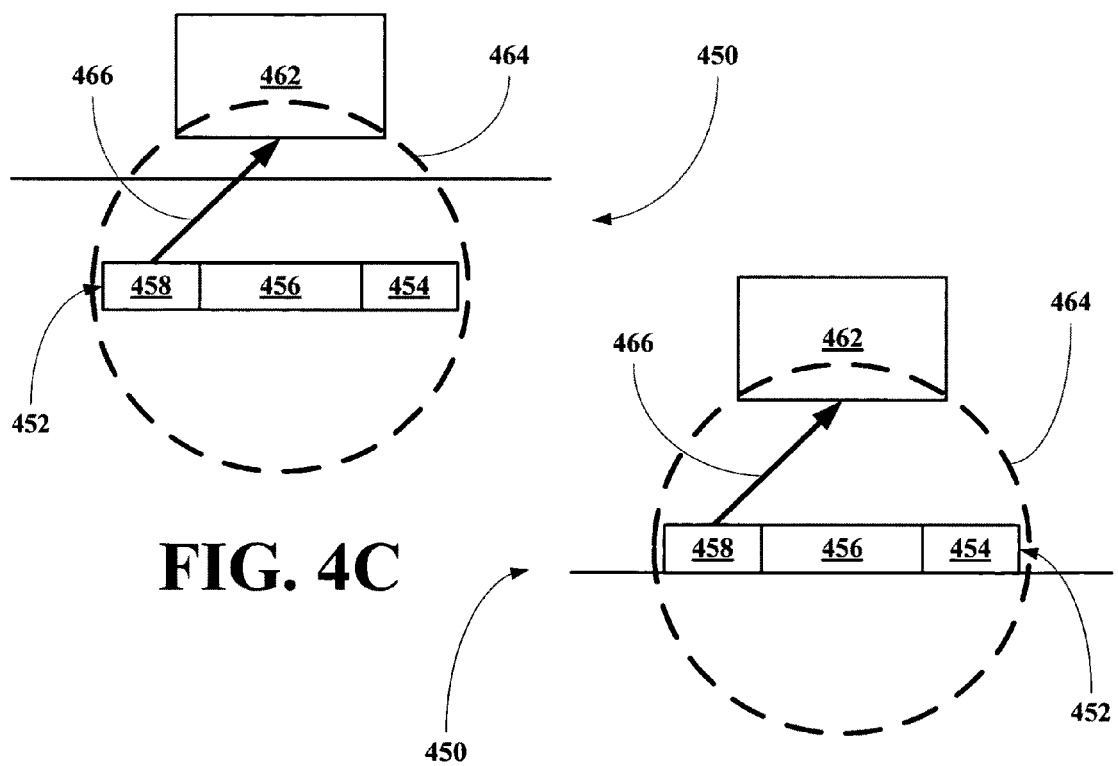
FIG. 4C
FIG. 4D

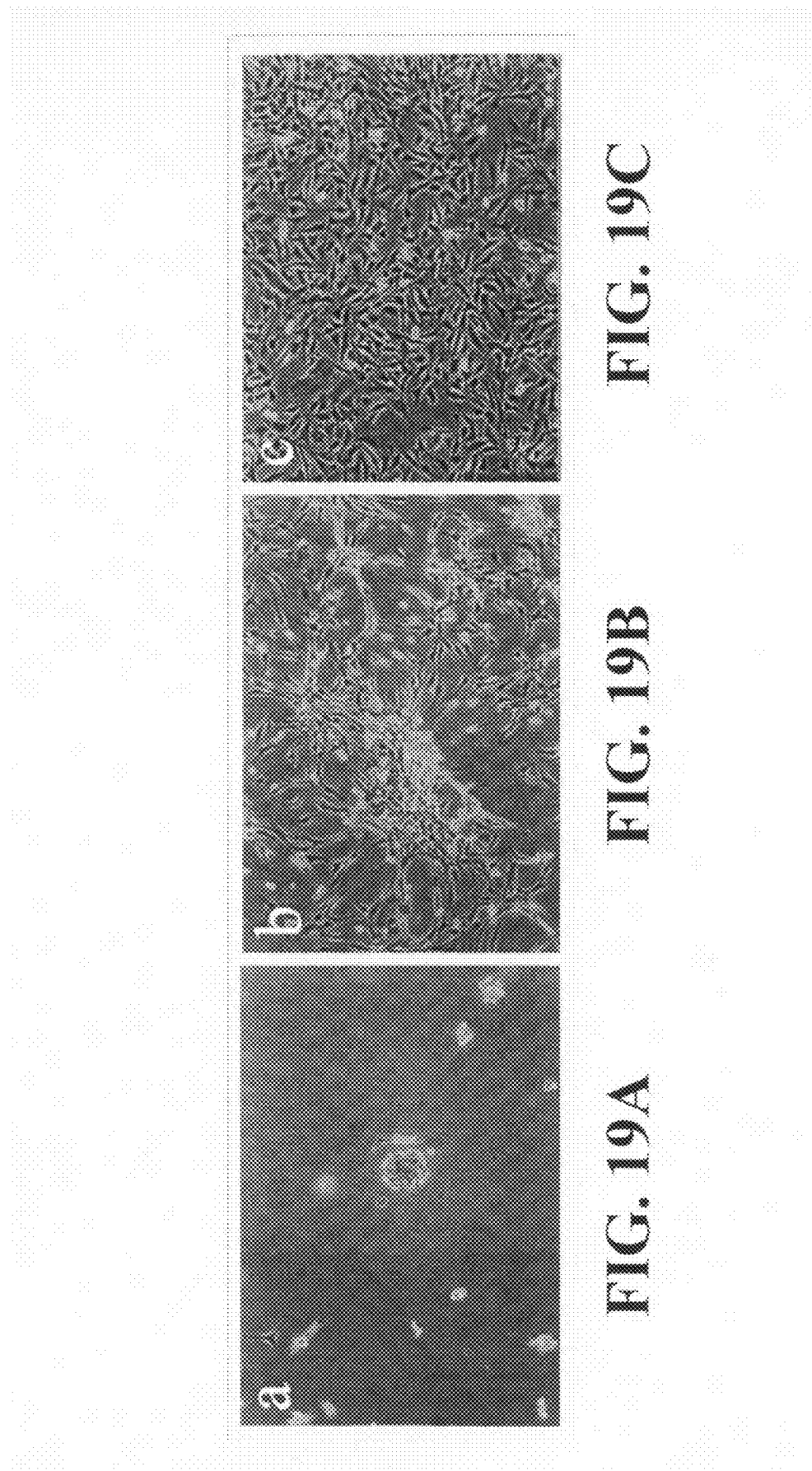

IMPLANTABLE BIOSENSOR FROM STRATIFIED NANOSTRUCTURED MEMBRANES

RELATED APPLICATIONS

This application claims provisional priority to U.S. Provisional Patent Application No. 60/368,921 filed Mar. 29, 2002.

GOVERNMENTAL SPONSORSHIP

Portions of the subject matter contained in this application was funded under one or more of the following governmental grants: NSF CAREER (CHE-9876265), AFOSR (F49620-99-C0072), NSF/NATO (NSF-NATO Grant # DGE-9902637), NSF Biophotonics Initiative (BES-0119483), and OCAST (AR99(2)-026), and NIH R21DK58380.

BACKGROUND OF THE INVENTION

1. Field of the Invention

The present invention relates to a new class of biosensors capable of sensing/monitoring at least one property of a biological system.

More particularly, the present invention relates to a new class of biosensors capable of sensing/monitoring at least one property of a biological system comprising a multi-layered structure having at least one sensing layer and at least one LBL layer, where the sensing layer and the LBL layer may be the same or different and to methods for sensing/monitoring the at least one property of the biological system and where the biosensors may be implantable or merely placed in contact with the biological system.

2. Description of the Related Art

In recent years, there have been extensive research and development efforts aimed at developing bio-sensors that can be reliably used for monitoring and quantifying changes in physiological, biochemical and/or morphological state of biological systems such as individual organs, tissues, or the body as a whole. The development of bio-sensors has been greatly advanced by recent developments in polymer technology and tissue engineering. A number of groups have reported successful deployment of polymer-based sensors for measurements of physiological and/or biochemical indicators such as glucose. The development of biomedical sensors have also benefited significantly from recent developments in the field of nanotechnology and its applications in medicine and biotechnology as well as developments in molecular recognition and molecular targeting techniques that can be incorporated into bio-sensors. The integration of these technologies provides an excellent opportunity for the development of new class of sensors that will utilize the latest developments in the fields of molecular and structural biology, polymer technology and nanotechnology. However, the application of polymer-based sensors in medicine could be limited due to the lack of specificity, lack of sufficient contrast for detection, lack of long term stability and lack of functionality that may limit the use of such sensors in continuous monitoring of biological systems.

When light interacts with a turbid medium such as skin, photons are either absorbed or redistributed in tissue via forward and backward scattering resulting in attenuation of light intensity [16]. The ability of a tissue to absorb and scatter light can be quantified by characterizing its optical properties mainly, the absorption ($\mu_a$) and scattering ($\mu_s$) coefficients [17]. These efforts have lead to the development of many promising diagnostic applications for optical spectroscopy and optical imaging in medicine.

The technical challenges associated with the development of a non-invasive sensor led to the development of implantable sensors for minimally invasive monitoring of different biological analytes (predominantly glucose).

Reversible and irreversible changes in the biochemical composition of tissue can lead to detectable changes in tissue properties such as the optical properties of tissue (i.e. optical pathlength) in various regions of optical spectrum (i.e., UV, Visible, Near infrared and infrared). In the near infrared region, changes in tissue scattering are more specifically attributed to the analyte as an osmolyte than changes in tissue absorption spectra. The scattering coefficient, $\mu_s$, and reduced scattering coefficient, $\mu_s'$, are dependent on the refractive index (n) mismatch between the extracellular fluid (ECF) and the cellular membranes as well as the morphology and dimensions of cells. In the near infrared spectral range, the index of refraction of the ECF is between about 1.348 and about 1.352, whereas the index of refraction of the cellular membranes and protein aggregates is in the range of about 1.350 to about 1.460. An increase in analyte concentration in the extracellular fluid increases its refractive index. Therefore, adding glucose to blood raises the refractive index of the ECF and consequently decreases the scattering coefficient of the tissue as a whole. This effect has been observed in tissue-simulating phantoms and in vivo using diffuse reflectance measurement systems. In these measurements, the optical signal that was monitored remotely came from photons that were diffusely reflected/backscattered from the scattering centers such as cells within tissue after they have traveled through a multi-layered, highly heterogeneous structure like skin and participated in a large number of scattering events before they could be detected. Thus, in these types of measurements where near-IR light propagation in tissue is dominated by scattering events, the detected glucose-induced changes in optical pathlength (scattering coefficient) of tissue only reflects an average change in the optical pathlength as function of glucose concentration and cannot be resolved spatially to provide a highly sensitive and specific assessment of the dependence of optical pathlength in tissue on glucose concentration. Additional fluctuations in the reported measurements are caused by the inability of these techniques to optically probe a predetermined region of the tissue for an accurate measurement of analytes in general, and blood glucose in particular, on a reproducible basis.

Approximately, 14 million people in the USA and more than 120 million people all over the world suffer from diabetes mellitus, a chronic systemic metabolic disease. Self-monitoring of blood glucose is the recommended treatment for all insulin dependent diabetic patients.[1,4] In addition, since the announcement of the Diabetes Control and Complications trial results, there is now no question that intensive management of blood sugars is an effective means to prevent or at least slow the progression of diabetic complications once present. Implementation of these intensive management strategies requires accurate and frequent self-monitoring of blood sugars. Unfortunately, it is frequently difficult to obtain the appropriate motivation and dedication on the part of the diabetic patients to successfully implement an intensive program of blood sugar monitoring. Reasons for the lack of compliance are numerous but include the pain associated with obtaining a blood sample and cost. In addition, there are a number of other illnesses that require constant monitoring of important biological intermediates, such as neurotransmitters, nitrogen oxides, hormones, enzymes, pH and other parameters. In each of these illnesses, invasive methods of analysis are typically utilized to monitor and control the illness. Again, these invasive methods involve taking and processing blood and/or other body fluids samples.

In the past two decades, there has been a strong effort towards the developments of noninvasively and minimally invasive techniques for quantifying blood chemicals, particularly glucose, using various optical approaches. These include fluorescence,[2,4] infrared absorption spectroscopy,[3,4,4,4] polarimetry,[5,4] and Raman spectroscopy.[6,4] As yet, none of these systems fully meets the expected performance nor have they achieved practical significance. Each system has associated limitations such as: (1) low sensitivity (signal-to-noise ratio) for the glucose concentrations at clinically relevant levels, and/or (2) insufficient specificity for glucose detection.

Current approaches to engineering of implantable sensors are predominantly focused on electrochemical devices. However, the electrochemical mode of monitoring necessitates external wires, which are both uncomfortable for the patient and may result in inflammation of the target tissue. The technical challenges associated with the development of a non-invasive glucose sensor have lead others to propose development of implantable sensors for minimally invasive monitoring of glucose. These sensors are polymer-based and are designed to respond to changes in glucose concentration by either swelling, altering the index of refraction, changing fluorescence characteristics or changing turbidity/optical clarity.[7,4-10,4] However, accurate quantitative assessment of changes under in vivo conditions has proven to be a challenge due to lack of optical contrast and/or lack of high specificity. For example, fluorescence spectroscopy has been pursued with the aim to develop an analyte-specific fluorescence probe that can be incorporated into an implantable sensor for remote sensing. However, issues related to the long-term stability of the fluorescence probe and the lack of reversibility of the response has significantly slowed the development of this promising approach.[25,4]

It is known that glucose can alter optical properties of tissue by reducing light scattering in tissue based on its properties as an osmolyte.[11,4] This effect was demonstrated in vivo using diffuse reflectance measurement.[11,4] However, due to a large number of scattering events that occur in tissue, the detected glucose-induced changes in optical pathlength reflect only an average change in the optical pathlength as a function of glucose concentration and can not be resolved spatially to provide a highly sensitive assessment of the dependence of optical pathlength in tissue on glucose concentration.

Thus, there is a need in the art for new, accurate and reliable implantable or tissue communicating biosensors for non-invasive or substantially non-invasive or minimally invasive monitoring of tissue characteristics and/or bodily fluid characteristics based on polymeric multi-layered composite constructs having properties (physical and/or chemical properties) capable of detection via optical, spectroscopic, optoacoustic, nmr, mri, ultrasonic, or other detection techniques, where a change in response of the biosensor corresponds to a change in concentration of a component of interest in the tissue and/or bodily fluid such as glucose.

SUMMARY OF THE INVENTION

Sensing and Detecting Apparatuses

The present invention provides an implantable or non-invasive or minimally invasive biocompatible sensing apparatus including at least one bio-sensor (i.e., a single bio-sensor or multiple bio-sensors within a single apparatus) adapted to sense changes in a biological system or monitor a biological system.

The present invention also provides an implantable or non-invasive or minimally invasive, biocompatible sensing apparatus including a bio-sensor, where the bio-sensor is adapted to undergo a change in a detectable property (physical and/or chemical) in response to a change in a concentration of a target atom, ion, molecule and/or molecular assembly in a target site in an animal including a human body.

The present invention also provides an implantable or non-invasive or minimally invasive, biocompatible sensing apparatus including a glucose sensor, where the glucose sensor is adapted to undergo a change in a detectable property in response to a change in a glucose concentration in a target site in an animal including a human body.

The present invention also provides an implantable or non-invasive or minimally invasive bio-compatible detecting apparatus including an excitation/probing source adapted to create an excitation/probing signal, at least one sensor having a property that varies in response to a change in a biological system and interacts with the excitation/probing signal to produce a response signal, a detector capable of detecting the response signal exiting the sensor and a communication component adapted to transmit the response signal out of the biological system.

The present invention also provides an implantable or non-invasive or minimally invasive bio-compatible detecting apparatus including an electromagnetic radiation source adapted to create an excitation electromagnetic spectrum, at least one sensor having a property that varies in response to a change in a biological system and interacts with the excitation spectrum to produce a response spectrum, a detector capable of detecting a response spectrum exiting the sensor and a communication component adapted to transmit the response spectrum out of the biological system.

The present invention also provides an implantable or non-invasive or minimally invasive bio-compatible detecting apparatus including an excitation/probing source adapted to create an excitation/probing signal, at least one sensor having a property that varies in response to a change in a concentration of an atom, ion, molecule and/or molecular assembly associated with a target site of an animal including a human and interacts with the excitation/probing signal to produce a response signal, a detector capable of detecting the response signal exiting the sensor and a communication component adapted to transmit the response signal out of the animal's body.

The present invention also provides an implantable or non-invasive or minimally invasive bio-compatible detecting apparatus including an electromagnetic radiation source adapted to create an excitation electromagnetic spectrum, at least one sensor having a property that varies in response to a change in a concentration of an atom, ion, molecule and/or molecular assembly associated with a target site of an animal including a human and interacts with the excitation spectrum to produce an response spectrum, a detector capable of detecting a response spectrum exiting the sensor and a communication component adapted to transmit the response spectrum out of the animal's body.

Sensing, Detecting and Monitoring Methods

The present invention provides a method for monitoring a biological system comprising the step of implanting a non-invasive or minimally invasive biocompatible sensing apparatus including at least one bio-sensor (i.e., a single bio-sensor or multiple bio-sensors within a single apparatus) in the biological system, where the apparatus is adapted to sense changes in the biological system. Once implanted, applying an excitation/probing signal to the implanted apparatus and detecting a response to the excitation/probing signal to produce an initial state or a present state of the biological system. The method can also include repeating the applying and detecting steps on an intermittent basis, a periodic basis, a continuous basis or a mixture or combination thereof to obtain a response profile. The method can also include the step of administering a pharmaceutical agent to adjust the state of the biological system and repeating the applying and detecting steps to monitor a response to the administered pharmaceutical agent.

The present invention also provides a method including the steps of implanting a non-invasive or minimally invasive, biocompatible sensing apparatus including a bio-sensor, where the bio-sensor is adapted to undergo a change in a detectable property in response to a change in a concentration of a target atom, ion, molecule and/or molecular assembly in a target site in an animal including a human body. Once implanted, applying an excitation signal to the implanted apparatus and detecting a value of the detectable property to produce an initial state or a present state of the target site. The method can also include repeating the applying and detecting steps on an intermittent basis, a periodic basis, a continuous basis or a mixture or combination thereof to obtain a response profile of the target site. The method can also include the step of administering a pharmaceutical agent to adjust the concentration of a target atom, ion, molecule and/or molecular assembly in the target site and repeating the applying and detecting steps to monitor a response to the administered pharmaceutical agent.

The present invention also provides a method for monitoring glucose concentrations in animals including humans including the steps of implanting a non-invasive or minimally invasive, biocompatible sensing apparatus including a glucose sensor in a target site of an animal including a human body, where the glucose sensor is adapted to undergo a change in a detectable property in response to a change in a glucose concentration in the target site, where the detectable property is detectable via optical, fluorescence, phosphorescence, magnetic (nmr or mri), acoustic (e.g., ultrasonics), optoacoustic, or any other detection system now in existence to yet developed. Once implanted, applying an excitation signal to the implanted apparatus and detecting a value of the detectable property to produce an initial state or a present state of the target site. The method can also include repeating the applying and detecting steps on an intermittent basis, a periodic basis, a continuous basis or a mixture or combination thereof to obtain a glucose response profile of the target site. The method can also include the step of administering an insulin-containing pharmaceutical agent to adjust the glucose concentration in the target site and repeating the applying and detecting steps to monitor a response to the administered insulin-containing pharmaceutical agent.

The present invention also provides a method for detecting a state of a biological system including the steps of implanting a non-invasive or minimally invasive bio-compatible detecting apparatus in the biological system, where the detecting apparatus includes an excitation source adapted to create an excitation signal, at least one sensor having a property that varies in response to a change in the biological system and interacts with the excitation signal to produce a response signal, a detector capable of detecting the response signal exiting the sensor and a communication component adapted to transmit the response signal out of the biological system. Once implanted, transmitting the response signal out of the biological system on an intermittent basis, a periodic basis, a continuous basis or a mixture or combination thereof to obtain a glucose response or response profile of the biological system. The method can also include the step of administering a pharmaceutical agent to adjust the biological system to a desired state and transmitting step to monitor a response to the administered pharmaceutical agent.

The present invention also provides a method for detecting a state of a biological system including the steps of implanting non-invasive or minimally invasive bio-compatible detecting apparatus in the biological system, where the apparatus includes an electromagnetic radiation source adapted to create an excitation electromagnetic spectrum, at least one sensor having a property that varies in response to a change in the biological system and interacts with the excitation spectrum to produce an response spectrum, a detector capable of detecting a response spectrum exiting the sensor and a communication component adapted to transmit the response spectrum out of the biological system. Once implanted, transmitting the response signal out of the biological system on an intermittent basis, a periodic basis, a continuous basis or a mixture or combination thereof to obtain a response or response profile of the biological system. The method can also include the step of administering a pharmaceutical agent to adjust the biological system to a desired state and transmitting step to monitor a response to the administered pharmaceutical agent.

The present invention also provides a method for detecting a state of a target site of an animal including a human including the steps of implanting a non-invasive or minimally invasive bio-compatible detecting apparatus in the target site, where the detecting apparatus includes an excitation source adapted to create an excitation signal, at least one sensor having a property that varies in response to a change in the target site and interacts with the excitation signal to produce a response signal, a detector capable of detecting the response signal exiting the sensor and a communication component adapted to transmit the response signal out of the target site. Once implanted, transmitting the response signal out of the target site on an intermittent basis, a periodic basis, a continuous basis or a mixture or combination thereof to obtain a glucose response or response profile of the target site. The method can also include the step of administering a pharmaceutical agent to adjust the target site to a desired state and transmitting step to monitor a response to the administered pharmaceutical agent.

The present invention also provides a method for detecting a state of a target site of an animal including a human including the steps of implanting non-invasive or minimally invasive bio-compatible detecting apparatus in the target site, where the apparatus includes an electromagnetic radiation source adapted to create an excitation electromagnetic spectrum, at least one sensor having a property that varies in response to a change in the target site and interacts with the excitation spectrum to produce an response spectrum, a detector capable of detecting a response spectrum exiting the sensor and a communication component adapted to transmit the response spectrum out of the target site. Once implanted, transmitting the response signal out of the target site on an intermittent basis, a periodic basis, a continuous basis or a mixture or combination thereof to obtain a response or response profile of the target site. The method can also include the step of administering a pharmaceutical agent to adjust the target site to a desired state and transmitting step to monitor a response to the administered pharmaceutical agent.

The preferred detecting apparatus include electronic components that measure the change in amplitude, phase, frequency or wavelength or a combination of these variables and are activated by an external field, where the excitation source or electromagnetic radiation source include electronic components that absorb power from the field to generate an excitation signal or spectrum and the detector absorbs power from the field to detect the response signal or spectrum and transmit the response signal or spectrum to an external receiver, which then converts the detected signal into a value corresponding to the detectable property of the sensor.

The present invention also provides a method for sensing, detecting and monitoring a state of a biological system including the steps of placing a biosensor of this invention, with or without built in simulation and detection hardware and software, in contact with the biological system in such a way that the biosensor can sense, detect and monitor the biological systems. Such an application is ideally suited for sensing changes in mucosal linings (gynecological tract, GI tract, oral tract, eyes, etc.)

DESCRIPTION OF THE DRAWINGS

FIGS. 1A&B depicts a schematic illustration of the process for preparing a LBL layer, FIGS. 1C&D depicts a schematic illustration of the process for preparing an LBL layer including nanoparticles or nonstructures, The invention can be better understood with reference to the following detailed description together with the appended illustrative drawings in which like elements are numbered the same:

FIG. 4A depicts a preferred embodiment of a detection system of this invention including a sensing apparatus of FIGS. 2A-P, FIG. 4A depicts another preferred embodiment of a detection system of this invention including a sensing apparatus of FIGS. 2A-P, FIG. 4C depicts a preferred embodiment of a detection system of this invention including a sensing apparatus of FIGS. 3A-D, FIG. 4D depicts another preferred embodiment of a detection system of this invention including a sensing apparatus of FIGS. 3A-D, Grant

NanoLett

Figure 15:
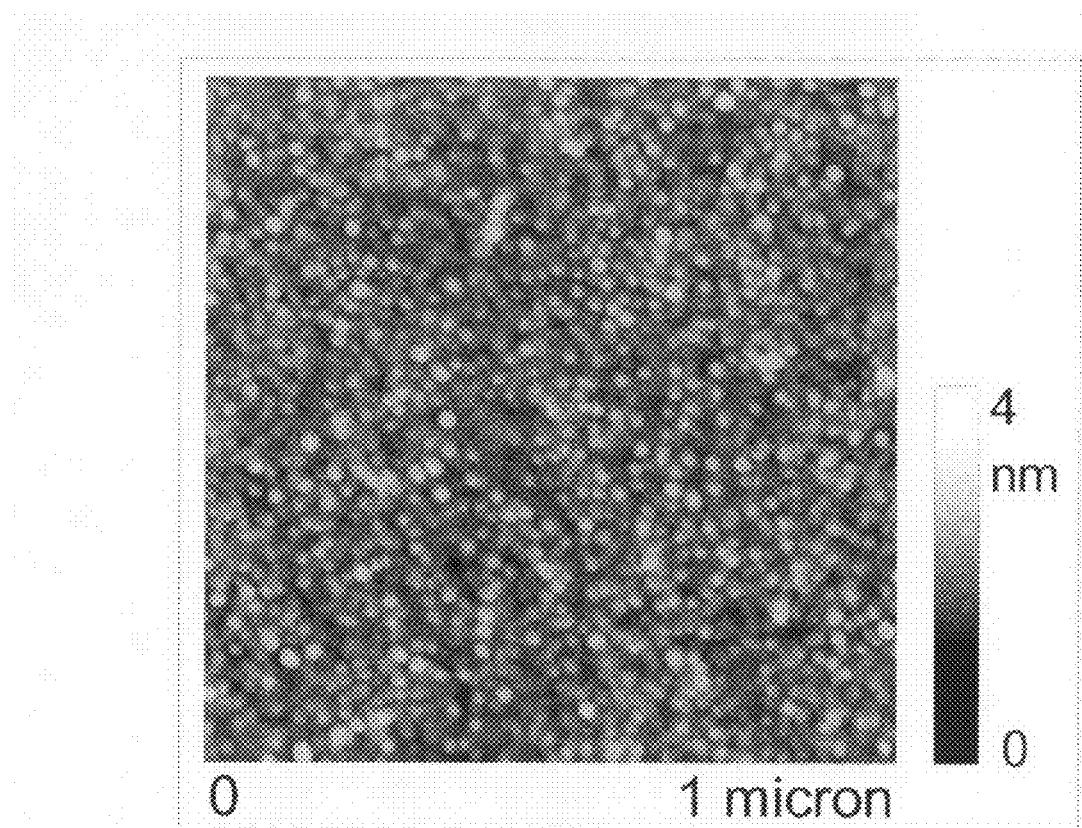
Figure 16:
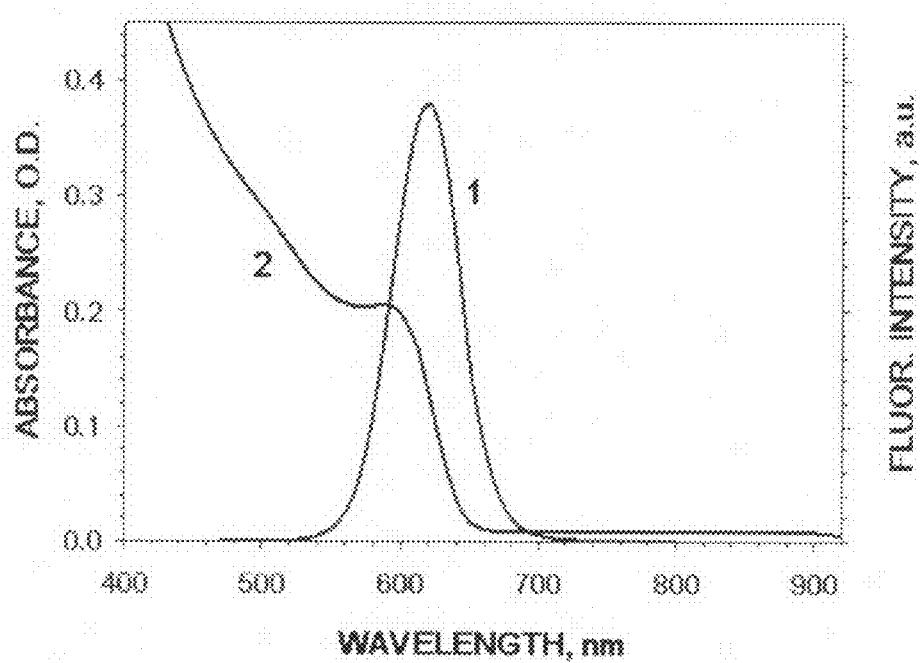
Figure 17:
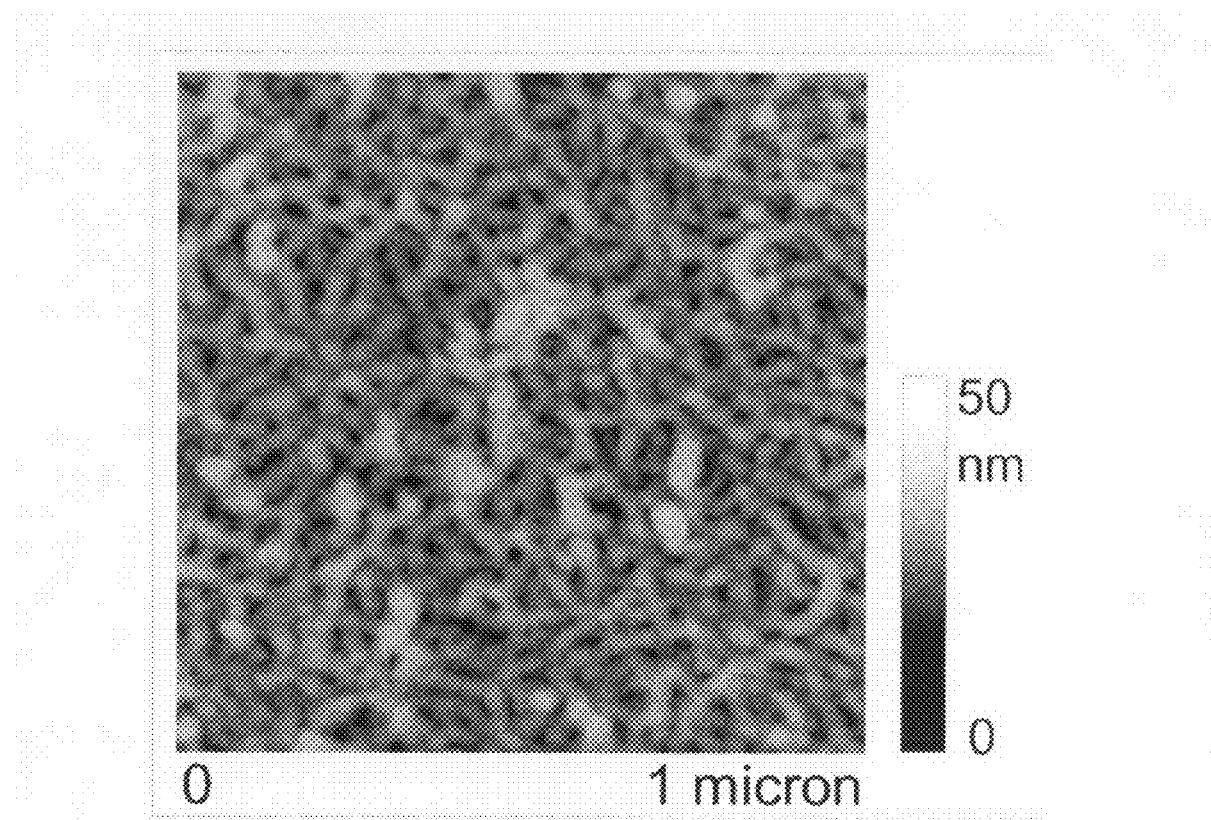
Figure 18:
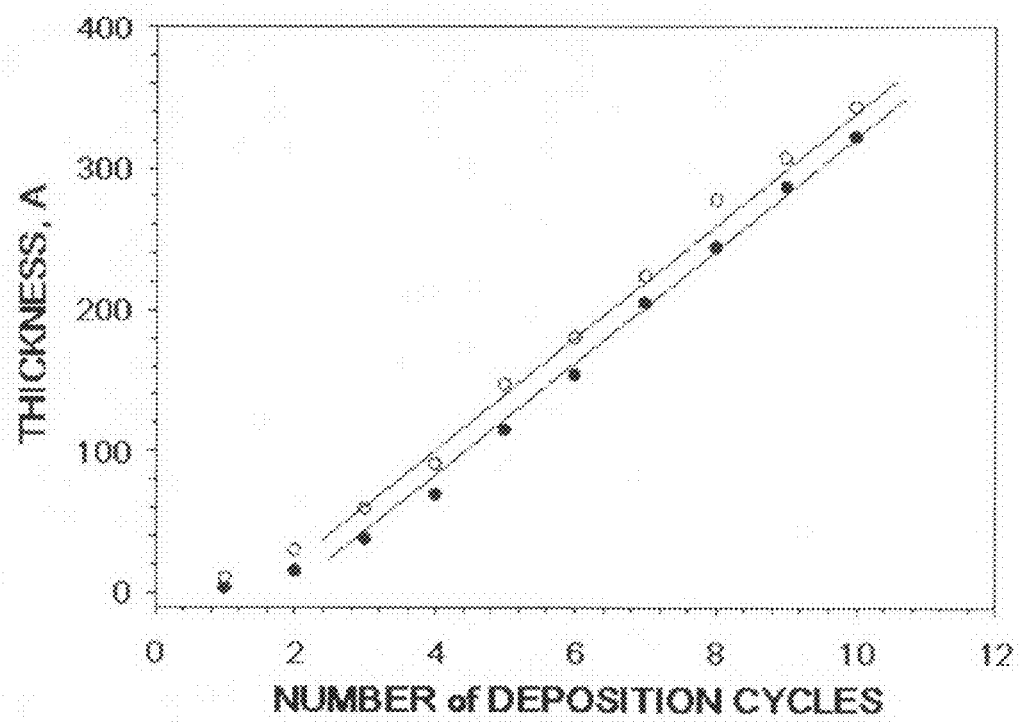

FIG. 15 depicts an AFM image of PDDA/CdTe bilayer,

FIG. 16 depicts Photoluminescence (1) and absorption (2) spectra of $(PDDA/CdTe)_{10}$ LBL assembled film, FIG. 17 depicts an AFM image of PDDA/PAA/collagen assembly, FIG. 18 depicts ellipsometric measurements of the thickness of $PDDA(PAA/collagen)_n$ multilayers, n=1-10, for collagen (closed circles) and PAA (open circles) layers vs. the number of adsorption cycles, n.

Figure 20A:
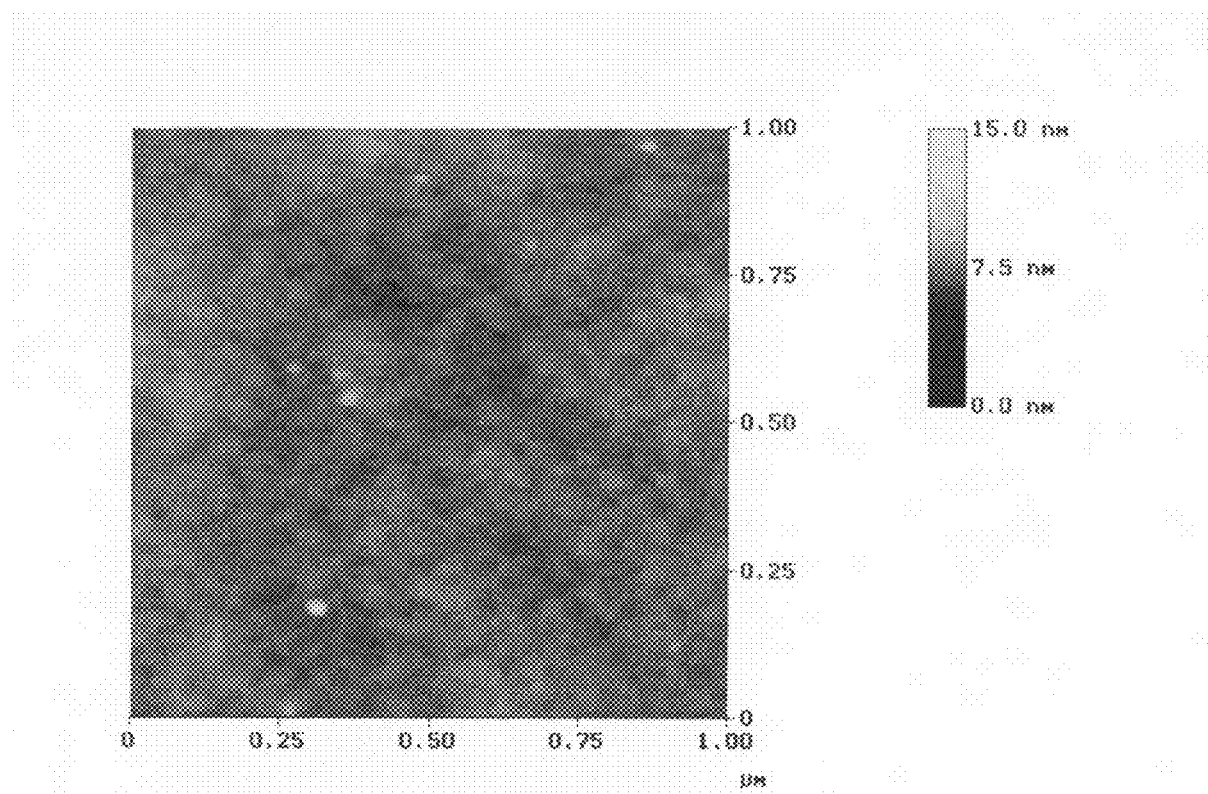
Figure 21:
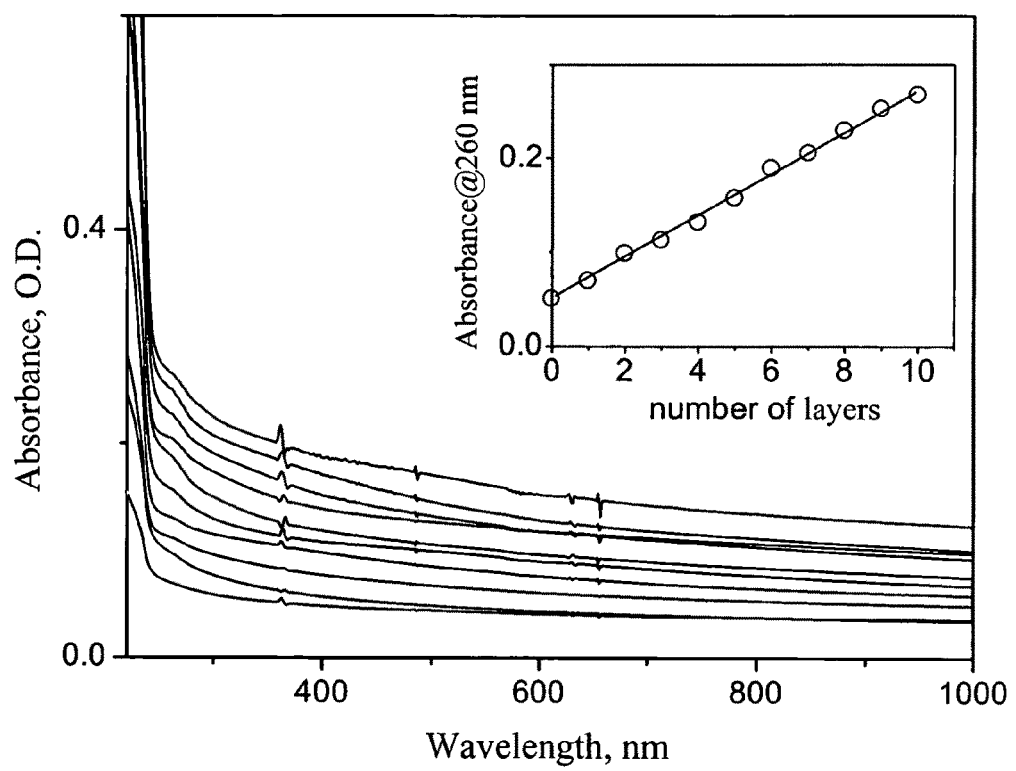

FIGS. 19A-C depicts optical microscopy images of C2C12 myoblast culture cells on the surface of (A) $(PDDA/CdTe)_3$, (B) $(PDDA/CdTe)_3PDDA(PAA/Collagen)_1$, and (c) $(PDDA/CdTe)_3PDDA(PAA/Collagen)_5$ LBL films LBL Figure Legends FIG. 20A&B depicts an AFM image of PDDA/PSS (a) and PDDA/PSS/collagen (b) assemblies FIG. 21 depicts a UV-vis spectra of sequentially adsorbed PDDA(PSS/collagen)$_n$ multilayers, n=1-10. The inset shows the dependence of absorbance at 260 nm vs. the number of deposition cycles, n.

Figure 22:
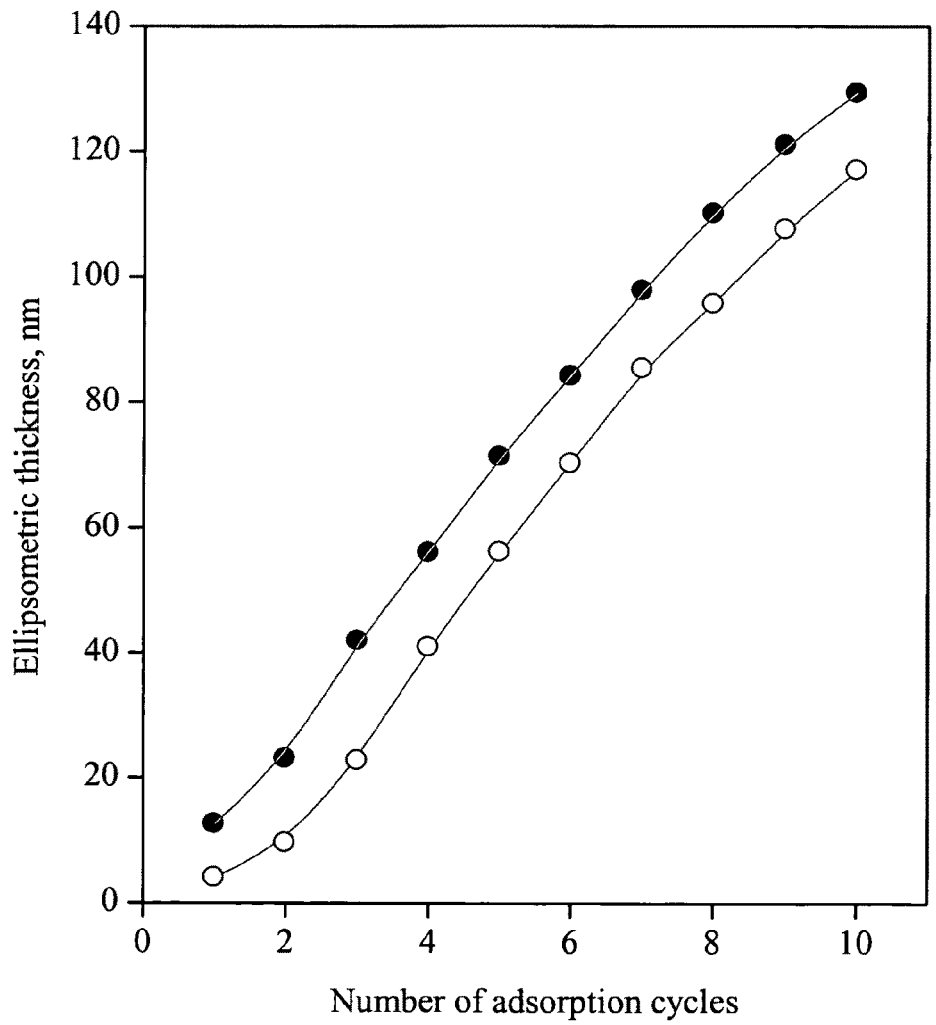

FIG. 22 depicts an Ellipsometric measurements of the thickness of PDDA(PSS/collagen)$_n$ multilayers, n=1-10, for collagen (closed circle) and PSS (open circle) layers vs. the number of adsorption cycles, n.

Figure 23:
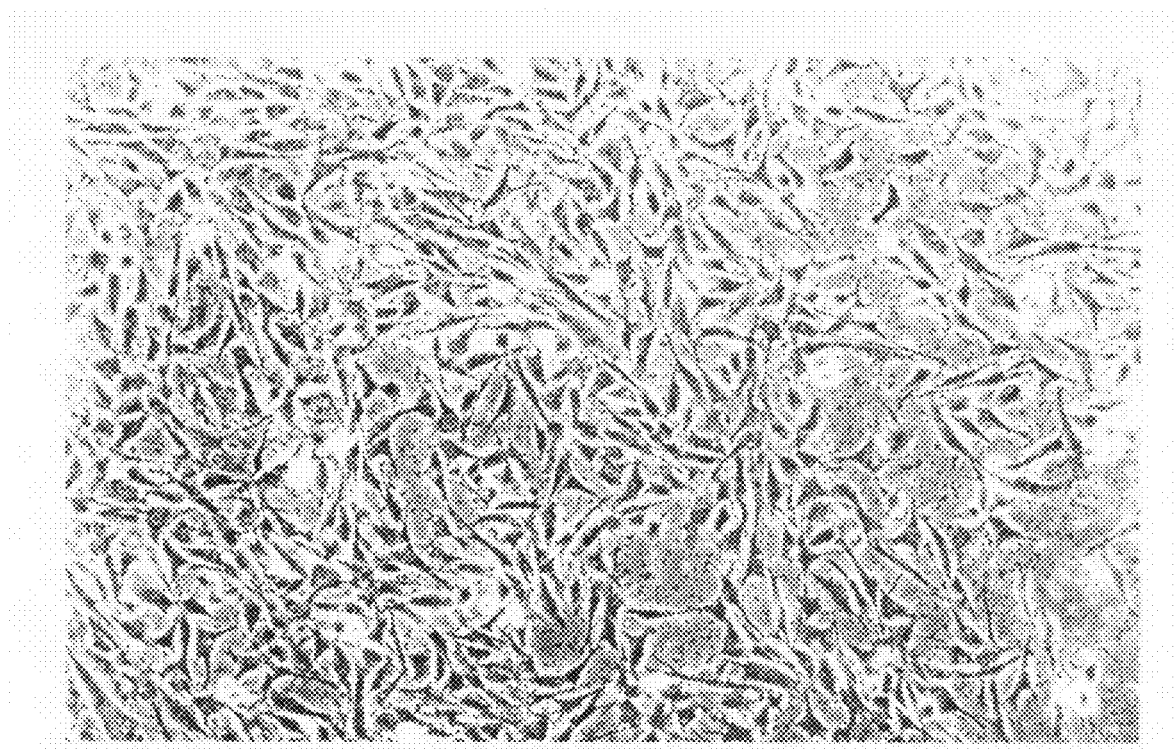

FIG. 23 depicts an optical microscope image (magnification 100×) of seeding muscle myoblast cells (C2C12) growing on substrates coated by PDDA(PSS/collagen)$_2$ multilayer in the presence of 15% FBS and 2% streptomycin/penicillin after 24 h.

Figure 24:
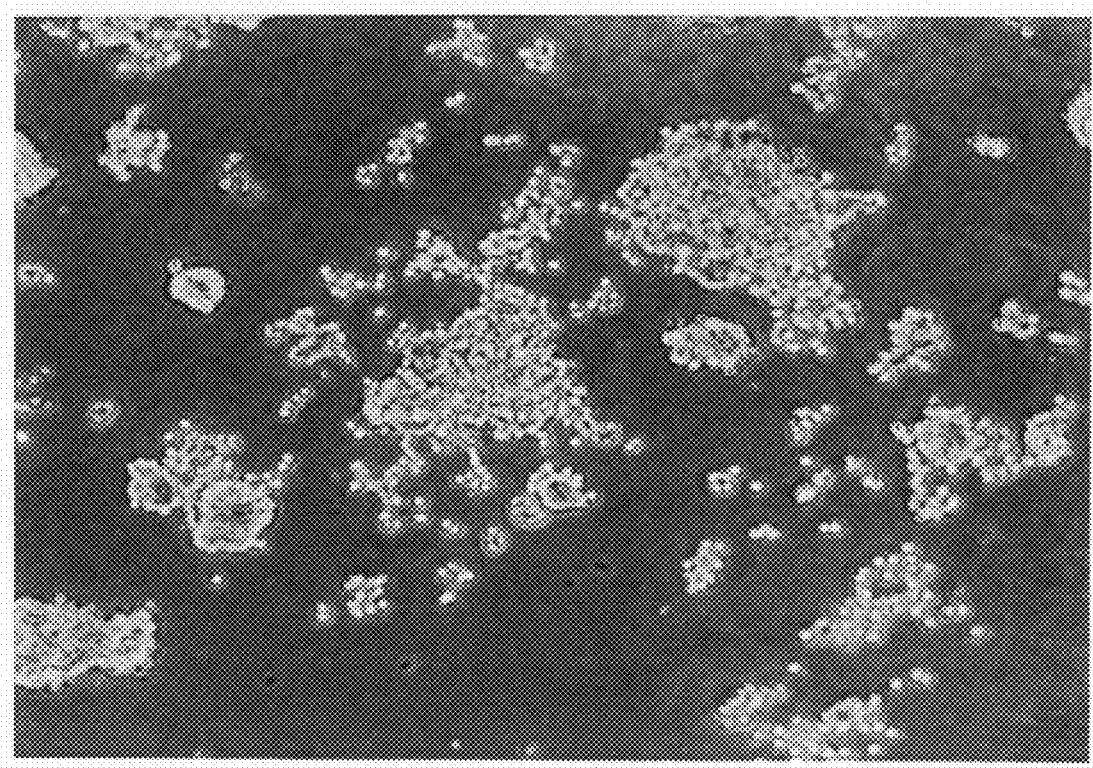

FIG. 24 depicts an optical microscope image (magnification 100×) of PC12 cells attached to substrates coated by PDDA(PSS/collagen)$_2$ multilayer in RPMI 1640 medium (GIBCO), containing 5% FBS, 10% horse serum (GIBCO), 2% streptomycin/penicillin after 24 h.

DETAILED DESCRIPTION OF THE INVENTION

The inventors have found that a new class of implantable or communicative biosensors can be constructed out of multi-layered polymeric composites, where at least one of the layers is an LBL layer and at least one of the layers undergoes a detectable property change in response to a change in a biophysical and/or biochemical environment surrounding the implanted biosensor. The inventors propose implantable or communicative membrane sensors that allow for a non-invasive or minimally invasive monitoring of tissue parameters or body parameters. While specific attention is paid to sensing glucose, the sensors can be constructed to respond to one or more analytes relevant for body functions. By changing its structure and/or sensing elements, the sensor can be altered to monitor any desire atom, ion, molecular, molecular assembly or mixtures and combinations thereof in a given tissue to monitor specific body parameters or distributed in the body to monitor global body parameters, where the term body parameter. The term communicative means that the biosensor is in physical and/or chemical communication with a biological system. For example, the biosensor can be placed in contact with the surface of an organ such as the skin, the eye, a mucosal lining (gynecological tract, GI tract, oral tract, etc.).

The inventors have also found that free-standing LBL films can be prepared which are suitable as ultrathin membranes with a variety of possible applications ranging from gas separation, sensors, micromechanical devices, and advanced catalysis to artificial cell walls and organs. Preparation of these free-standing LBL films from inorganic colloids affords a rich palette of mechanical, chemical, molecular, optical, spectroscopic, electrical, and magnetic properties that can be imparted to the films. Importantly, the layer-by-layer mode of their preparation makes possible a degree of structural organization of such membranes, which is difficult to attain using other traditional production methods.

The inventors have also found that the LBL assembly method can be used to construct simple stratified composites that impart biocompatibility to films composed of nano-particles including semiconductor NPs. For example, a collagen-based layer deposited on top of a layer including CdTe nanoparticles (NPs) makes the NPs suitable for interfacing with tissues and cell cultures.

The responsive layer and LBL layer can each represent a layer that undergoes changes in physical and/or chemical properties in response to a change in the physical and/or chemical properties of the biological system in which it is in contact or implanted. Suitable responsive layer include, without limitation, any polymeric material (synthetic or biological) that undergoes a physical and/or chemical change in response to a change in a given physical and/or chemical property of the biological system. Exemplary examples of synthetic materials include hydrogel. Exemplary examples of biological materials include corneas, cartilage, or other naturally occurring hydrogels.

Features that distinguish the biosensor membrane apparatuses of this application from other implantable biosensor membrane or non-membrane apparatuses include at least: (1) the universality of the membrane biosensor preparation regardless of the detection method; (2) the ease of construction of multi-functional biosensor membrane apparatuses; (3) the ease of optimization of biosensor operations depending on analyte and biosensor placement; (4) the ease of construction of biosensor apparatuses including a single analyte/property sensor or multiple analyte/property sensors; and (5) the ease of construction of biosensor apparatuses having internal referencing.

These features are introduced into the biosensors using layer-by-layer (LBL) assembly processing for the formation of at least one layer of the biosensor membrane and/or the inclusion of at least one nanostructured material in at least one LBL layer of a composite (multi-layered) biosensor structure.

The sensors of this invention can be utilized in the following fields of use: (1) medical biosensors for continuous and intermittent monitoring of important biomolecules, for example glucose, NO, ionic strength, pH, hormone level, etc.; (2) battlefield military applications for sensing agents such as biological and chemical agents; (3) drug delivery and monitoring of drug consumption; (4) monitoring of functioning of other implants such as pace-makers; and (5) sensing mechanisms.

The changes in the implantable sensors can be monitored and quantified by a variety of optical, spectroscopic, electrical, magnetic and acoustic sensing and imaging techniques including, without limitation, (1) photoinduced or otherwise externally stimulated luminescence, (2) chemiluminescence; (3) polarization; (4) fluorescence spectroscopy; (5) absorption and reflectance spectroscopy; (6) optical coherent tomography; (7) Raman scattering and surface enhanced Raman scattering (SERS); (8) interferometric measurements; (9) multiwavelength and ratiometric measurements; (10) evanescent wave spectroscopy; (11) multiwavelength spectroscopies; (12) Bragg diffraction spectroscopy; (13) electrical capacitance measurements; (14) impedance spectroscopy; (15) potentiometric detection; (16) piezoelectric detection; (17) optoacoustic imaging and spectroscopy; (18) ultrasound imaging and spectroscopy; and (19) etc.

The proposed implants can be placed in the vicinity of the organ or the device and the readings will be taken remotely by the electrochemical means or microwave or radio-frequency stimulation. It should be noted that these implantable sensors are not limited to the above sensing implementations and that others may also be used.

Manufacturing of Implantable Sensors

Thin (polymer) membranes for optical sensing, while providing the convenience and sensitivity of analyte monitoring, are difficult to make for long-term in vivo applications because of fouling and strong immune response of the body to polymers enabling optical detection. The manufacturing of such membranes is typically accomplished via solvent casting, spin-casting or solvent processing of solidified pre-made prototypes. These techniques do not allow for the accurate stratification of the membrane nor for sufficient control of chemical and biological properties.

A new thin film deposition technique termed layer-by-layer assembly (LBL) significantly improves the quality of the membranes and impart multi-functional capabilities to them. LBL is based on the sequential adsorption of oppositely charged macromolecular species.[14.4] The driving force for LBL is the electrostatic attraction between positive and negative charges located on the solid surface and polyelectrolytes, colloids and other species in solution. Alternation of layers of positively and negatively charged components is the key principle of the layer-by-layer assembly.[15.4] Due to the monomolecular nature of the layers deposited in each cycle, the LBL technique affords nm scale precision in thin film thickness. Being quite simple and effective, LBL has been applied to a variety of charged species from classical inorganic colloids[16.4-18.4] to DNAs[19.4]. Importantly, the assembled biopolymers retain their 3D structure and biological activity[20.4] which can be used for enhancing biocompatibility of the LBL assembled materials and allows for the preparation of membranes of high complexity with nanometer scale accuracy in film thickness. This invention takes advantage of this technique in producing functional membranes for sensing of biomolecules.[21.4] The most common system used for LBL is a combination of poly(diallyldimethylammonium) polycation (PDDA) and a negatively charged organic or inorganic counterpart. Each deposition cycle produces a double layer consisting of a sub layer of PDDA and a monolayer of a colloid. The thickness of the polyelectrolyte layers ranges from 0.5-5 nm. The thickness of NP layer is close to the particle diameter (from 2 to 30 nm).[22.4]

Layer-by-Layer Assembly

The layer-by-layer assembly is usually realized as the sequential (mono)layer adsorption positively and negatively charged species: say A and B, by alternative dipping a substrate into a solution of A or a solution of B. For example, positively charged polyelectrolytes (PE) 100 are readily adsorbed to the surfaces of glass, quartz, silica, metals and most other materials 102 due to natural negative charge or existence of oxidation layer as shown again in FIG. 1A. Rinsing with a solvent 104—commonly water—between the adsorption steps removes the excess of the previous solution and leaves a thin (mono)layer of A species 106 on the surface as shown in FIG. 1B. Once the A layer has been applied to the substrate, the A coated substrate is dipped in a solution of B to form a B layer on top of the A layer and rinsed in a solvent, in a repeat of the steps shown in FIGS. 1A&B. Electrostatic and van der Waals attraction between the layer of A and oppositely charged partner B promotes its adsorption to the substrate. This cycle (film formation/rinsing) can be repeated as many times as required or necessary to reach the desirable thickness of the multilayers. The recurrent nature of the process makes it very attractive for both laboratory and industrial implementations.

Commonly, A and B are chosen to be of relatively high molecular weight, where Van der Waals interactions increase with molecular mass and the number of points of contact between molecules of A and molecules of B increasing the strength of the attraction between the A and B layers and rendering the absorption sufficiently irreversible to allow for the deposition of the next layer. Either A or B is almost always a PE, while the other LBL partner can be a dispersion of nanoparticles (NP), clay sheets, proteins, dyes, vesicles, DNA, viruses or other species 108 as shown in FIGS. 1C&D. Of course, once the NP containing layer 110 is formed, the substrate is generally washed as shown in FIG. 1B. The omnipresence of PEs in the most recent LBL assemblies is explained by their ability to cover irregularities owing to the rod-like conformation of the charged macromolecules in aqueous solutions. The LBL layers or responsive layers can include a marker that undergoes a property change in response to a change in concentration of target agent associated with the biological system, where the marker is selected from the group consisting of dyes, fluorescent dyes, fluorescent donor-acceptor pairs, dyes capable of undergoing FRET, Raman tags, nmr/mri tags, particles with variable indexes of refraction or polarization, or any other property that is capable of being detected and measure in a quantitative, qualitative or semi-quantitative manner or mixtures or combinations thereof.

Design of the Biosensor

In general, the proposed sensor with single or multianalyte capabilities (multi-sensor) can be described as a stratified membrane: symmetric or asymmetric with a minimum of two distinct strata responsible for different functionalities of the membrane. As film stratification in this invention, the structure can be represented by a sequence of different layers organized according to the purpose of the membrane. Some degree of layer interpenetration may exist and thickness of the strata may change significantly, however, in the middle points of the strata the chemical composition will be different from each other. The functionalities of the strata include, without limitation, biosensing, biocompatibility, ion sieving, biorecognition, remote bioactivation and stimulation and other functions improving selectivity, non-thrombogenicity, mechanical strength, conductivity, optical attenuation, pre-concentration and others. The sensor may provide either one or a combination of the functions as described herein.

Generally, biosensor membranes of this invention will have between about three and about five stratum to provide sufficient sensing capability, biocompatibility and structural integrity. In certain applications, the basic membrane can be coated with additional layer(s) imparting biocompatibility, such as collagen, fibrin, poly(lysine), poly(acrylic acid, poly (lactic acid), and other suitable biological layers with more biocompatible properties. Different manufacturing processes can be utilized in its preparation, however some of the strata will always be prepared by the layer-by-layer assembly technique.

Biosensors Formed Using LBL and Non-LBL Layer Formation

One preferred manufacturing approach for designing the stratified membrane biosensors of this invention starts from the LBL layer assembly process on a removable substrate, where the substrate can be dissolved, melted, delaminated or otherwise separated from the film after it is assembled. During this step, nanocolloids, polyelectrolyte, proteins, DNA, RNAs, oligonucleotides, organic and inorganic fibers or any other material or species suitable for LBL assembly can be incorporated into the LBL layers being formed on the substrate. Generally, the outer layer of the biosensors of this invention are LBL layers. After the LBL assembly, a central layer is coated on top of the prepared LBL film. This layer can be an LBL layer or a layer prepared by any other suitable technique such as, without limitation, such as sol-gel or polymerization, or painting, or spin coating, etc. This stratum may include biosensitive species responsible for transduction of the signal related to their concentration in the ambient media into a detectable signal such as an optical or spectroscopic signal. The biosensitive species can possibly be proteins, nucleotides, NPs or other natural or chemically synthesized compounds with specific affinity to analytes of interest, and carrier objects such as polymers or colloids modified by these species. The central layer can also exhibit a certain degree of organization such as packing of the biosensitive species or their carriers relevant for the optical or spectrocopic registration methods. The central layer can also include slow-release particles such as biodegradable capsule providing supplementary chemicals for the long-term operation.

After the deposition of the central layer, the substrate on which the assembly was performed is dissolved, melted, delaminated, or otherwise removed. The separated stratified thin film can then be simply folded so that the center layer is covered from both sides by the outer layers, which will result in the projected three-stratum sensing membrane. After that it may be cut to appropriate length, rolled, or processed otherwise to make it suitable for implantation. In addition, the prepared membrane can be overcoated with the biocompatibility layer(s). This layer will be transparent for the diffusion permeation of the analyte to the sensing layer(s). Although, this folding process in one preferred manufacturing technique, the more preferred techniques is simply to deposit an outer LBL layer on top of the center layer to form a three layer composite structure. Using either the folding process or the multi-layer formation process, many different biosensor composition structures can be formed. The following embodiment of biosensors of this invention illustrate some of the multitude of possible structures that can be produced using an combination of LBL and traditional layer forming processes.

Figure 2A:
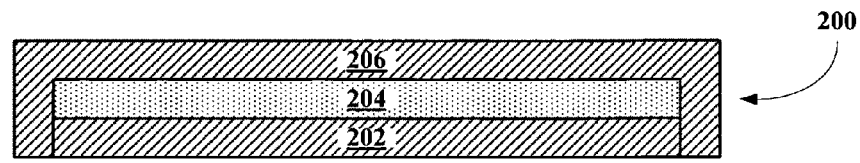
FIG. 2A depicts a preferred embodiment of a sensing apparatus of this invention.

Referring now to FIG. 2A, another preferred embodiment of a composite (layered) biosensor of this invention, generally 200 is shown to include a first LBL layer 202, a responsive layer 204 adapted to change a physical and/or chemical property in response to a change in a target atom, ion, molecule or molecular assembly associated with a biological system and a second LBL layer 206. Due to the process for making the LBL composites, the first layer 202 and the responsive layer 204 can be formed in a standard stack arrangement, while the second LBL layer 206 forms on all exposed surfaces of the partially formed construct of the layers 202 and 204. In this construct, the LBL layer 202 and 206 include ingredients such as nanoparticles, dyes, or other materials that improve detection of a detectable property of the composite, while the responsive layer 204 is adapted to change the detectable property in response to a change in the chemical and/or physical environment of the site of implantation in a biological system or in physical and/or chemical communication with the biological system.

Figure 2B:
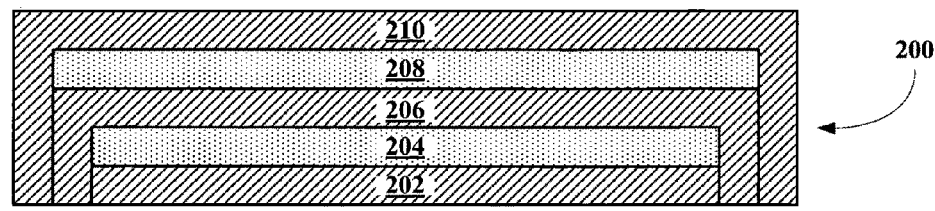
FIG. 2B depicts another preferred embodiment of a sensing apparatus of this invention.

Referring now to FIG. 2B, another preferred embodiment of a composite biosensor of this invention, 200, is shown to include a first LBL layer 202, a first responsive layer 204, a second LBL layer 206, a second responsive layer 208 and a third LBL layer 210. In this construct, the two responsive layers 204 and 208 can be the same or different as can be the LBL layer 202, 206 and 210. If the responsive layers 204 and 208 are the same, the combined single will be enhanced improving the signal-to-noise ratio and improving detection. If the responsive layers 204 and 208 are different, then this biosensor 200 can be used to simultaneously measure two different properties of a biological system, such as glucose, hemoglobin, glycated or glycosated hemoglobin, or other blood or bodily fluid components. In such a case, the responsive layer can be constructed to allow blood flow between the LBL layer by cutting or drilling holes in the layer or by placing capillary tube on the substrate during layer construction or the layer can be made sufficiently porous to allow red blood cells to pass between the LBL layers.

Figure 2C:
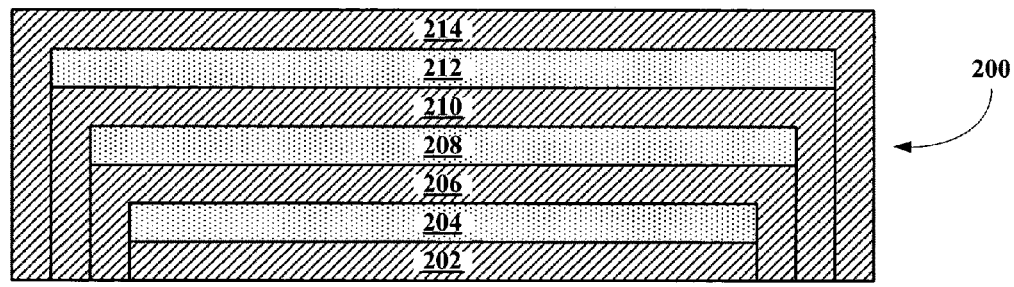
FIG. 2C depicts another preferred embodiment of a sensing apparatus of this invention.

Referring now to FIG. 2C, another preferred embodiment of a composite biosensor of this invention, 200, is shown to include a first LBL layer 202, a first responsive layer 204, a second LBL layer 206, a second responsive layer 208, a third LBL layer 210, a third responsive layer 212, and a fourth LBL layer 214. Again, each LBL layer can be the same or different and each responsive layer can be the same or different.

Figure 2D:
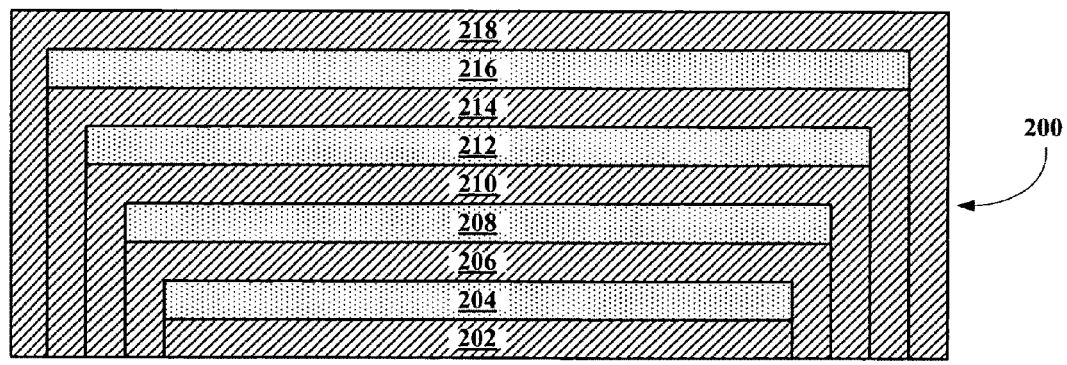
FIG. 2D depicts another preferred embodiment of a sensing apparatus of this invention.

Referring now to FIG. 2D another preferred embodiment of a composite biosensor of this invention, 200, is shown to include a first LBL layer 202, a first responsive layer 204, a second LBL layer 206, a second responsive layer 208, a third LBL layer 210, a third responsive layer 212, a fourth LBL layer 214, a fourth responsive layer 216 and a fifth LBL layer 218. Again, each LBL layer can be the same or different and each responsive layer can be the same or different.

Open Edge Biosensors Formed Using LBL and Non-LBL Layer Formation

Figure 2E:
FIG. 2E depicts another preferred embodiment of a sensing apparatus of this invention.

Referring now to FIG. 2E, preferred embodiment of a composite (layered) biosensor of this invention, generally 220 is shown to include a first LBL layer 222, a responsive layer 224 adapted to change a physical and/or chemical property in response to a change in a target atom, ion, molecule or molecular assembly associated with a biological system and a second LBL layer 226.

Figure 2F:
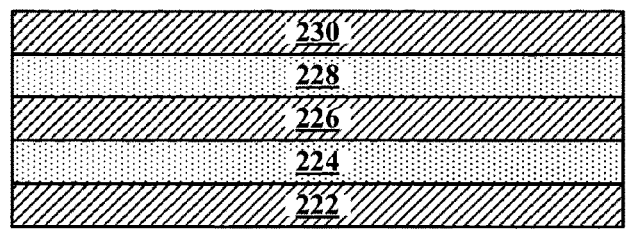
FIG. 2F depicts another preferred embodiment of a sensing apparatus of this invention.
Figure 2G:
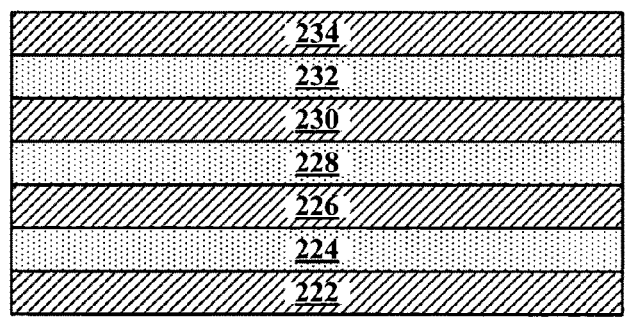
FIG. 2G depicts another preferred embodiment of a sensing apparatus of this invention.
Figure 2H:
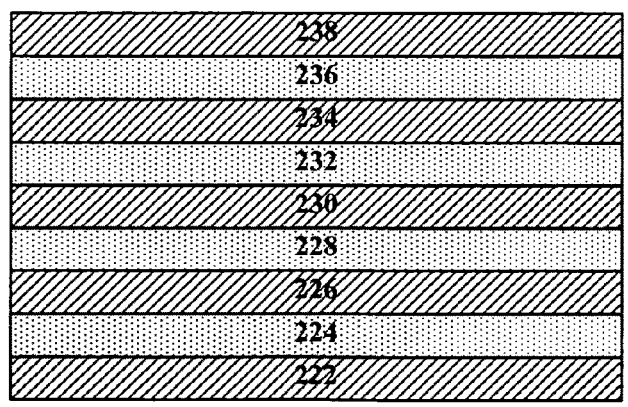
FIG. 2H depicts another preferred embodiment of a sensing apparatus of this invention.

Referring now to FIG. 2F, another preferred embodiment of a composite biosensor of this invention, 220, is shown to include a first LBL layer 222, a first responsive layer 224, a second LBL layer 226, a second responsive layer 228 and a third LBL layer 230. In this construct, the two responsive layers 224 and 228 can be the same or different as can be the LBL layer 222, 226 and 230.

Referring now to FIG. 1G, another preferred embodiment of a composite biosensor of this invention, 220, is shown to include a first LBL layer 222, a first responsive layer 224, a second LBL layer 226, a second responsive layer 228, a third LBL layer 230, a third responsive layer 3, and a fourth LBL layer 5. Again, each LBL layers can be the same or different and each responsive layers can be the same or different.

Referring now to FIG. 1H, another preferred embodiment of a composite biosensor of this invention, 220, is shown to include a first LBL layer 222, a first responsive layer 224, a second LBL layer 226, a second responsive layer 228, a third LBL layer 230, a third responsive layer 232, a fourth LBL layer 234, a fourth responsive layer 7 and a fifth LBL layer 9. Again, each LBL layers can be the same or different and each responsive layers can be the same or different.

Open Edge with End Cap Biosensors Formed Using LBL and Non-LBL Layer Formation

Figure 2I:
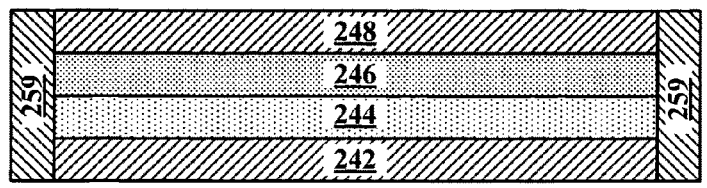
FIG. 2I depicts another preferred embodiment of a sensing apparatus of this invention.

Referring now to FIG. 2I, another preferred embodiment of a composite biosensor of this invention, generally 240, is shown to include a first LBL layer 242, a first responsive layer 244, a second responsive layer 246 and a second LBL layer 248. The biosensor 240 also includes end caps 259, which can be coated on, pressed on or applied in any other technique known in the art. Again, each LBL layers can be the same or different and each responsive layers can be the same or different.

Figure 2J:
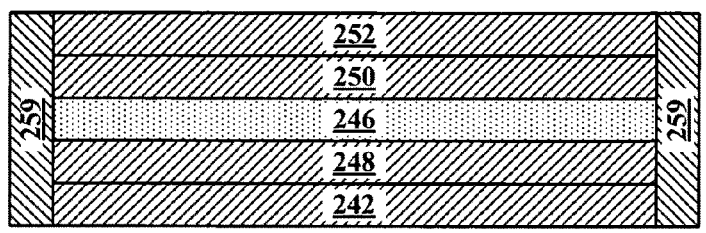
FIG. 2J depicts another preferred embodiment of a sensing apparatus of this invention.

Referring now to FIG. 2J, another preferred embodiment of a composite biosensor of this invention, generally 240, is shown to include a first LBL layer 242, a second LBL layer 248, a responsive layer 244, a third LBL layer 250, and a fourth LBL layer 252. The biosensor 240 also includes end caps 259, which can be coated on, pressed on or applied in any other technique known in the art. Again, each LBL layers can be the same or different and each responsive layers can be the same or different.

Figure 2K:
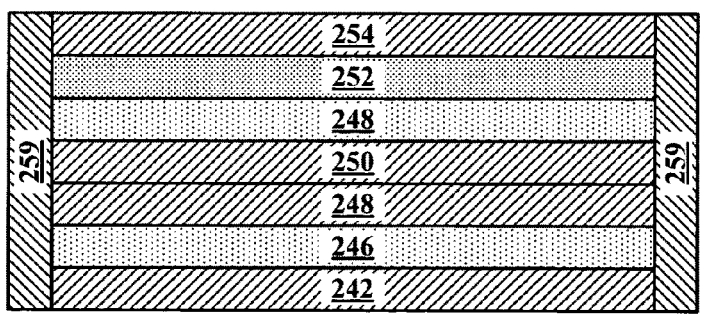
FIG. 2K depicts another preferred embodiment of a sensing apparatus of this invention.

Referring now to FIG. 2K, another preferred embodiment of a composite biosensor of this invention, generally 240, is shown to include a first LBL layer 242, a first responsive layer 244, a second LBL layer 248, a third LBL layer 250, a second responsive layer 246, a third responsive layer 254, and a fourth LBL layer 252. The biosensor 240 also includes end caps 259, which can be coated on, pressed on or applied in any other technique known in the art. Again, each LBL layers can be the same or different and each responsive layers can be the same or different.

Figure 2L:
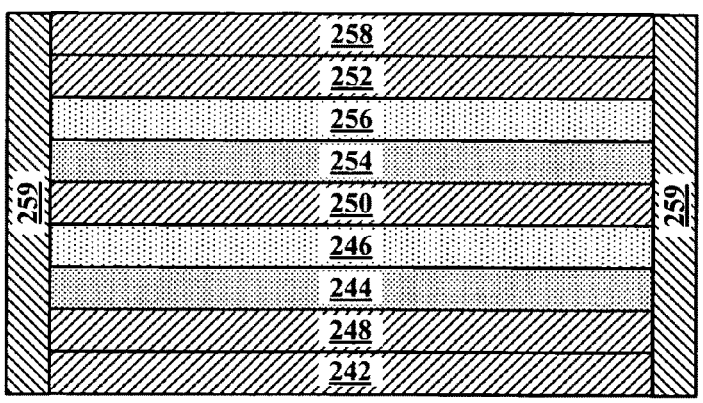
FIG. 2L depicts another preferred embodiment of a sensing apparatus of this invention.

Referring now to FIG. 2L, another preferred embodiment of a composite biosensor of this invention, generally 240, is shown to include a first LBL layer 242, a second layer 248, a first responsive layer 244, a second responsive layer 246, a third LBL layer 250, a third responsive layer 254, a fourth responsive layer 256, a fourth LBL layer 252 and finally a fifth LBL layer 258. The biosensor 240 also includes end caps 259, which can be coated on, pressed on or applied in any other technique known in the art. Again, each LBL layers can be the same or different and each responsive layers can be the same or different.

Coated/Encased Biosensors Formed Using LBL and Non-LBL Layer Formation

Figure 2M:
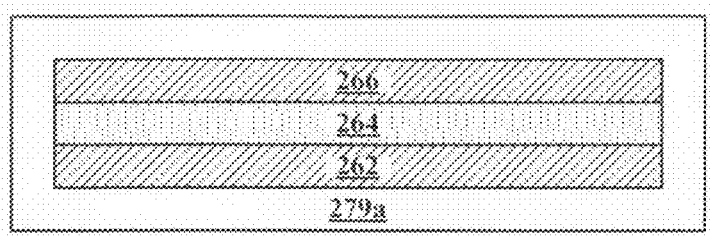
FIG. 2M depicts another preferred embodiment of a sensing apparatus of this invention.

Referring now to FIG. 2M, another preferred embodiment of a composite biosensor of this invention, generally 260, is shown to include a first LBL layer 262, a responsive layer 264 and a second LBL layer 266 all surrounded or encased by a coating 279a. Again, each LBL layers can be the same or different and each responsive layers can be the same or different.

Figure 2N:
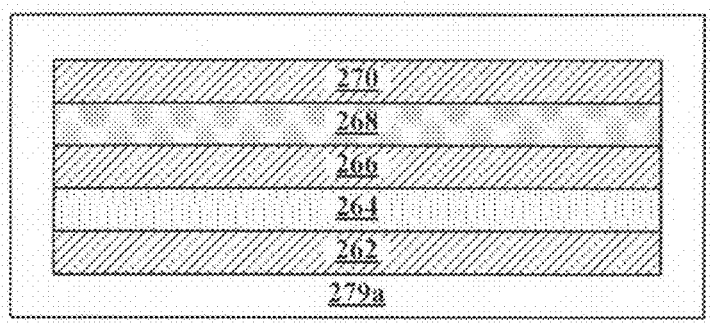
FIG. 2N depicts another preferred embodiment of a sensing apparatus of this invention.

Referring now to FIG. 2N, another preferred embodiment of a composite biosensor of this invention, generally 260, is shown to include a first LBL layer 262, a first responsive layer 264, a second LBL layer 266, a second responsive layer 268 and a third LBL layer 270 all surrounded or encased by a coating 279a. Again, each LBL layers can be the same or different and each responsive layers can be the same or different.

Figure 2O:
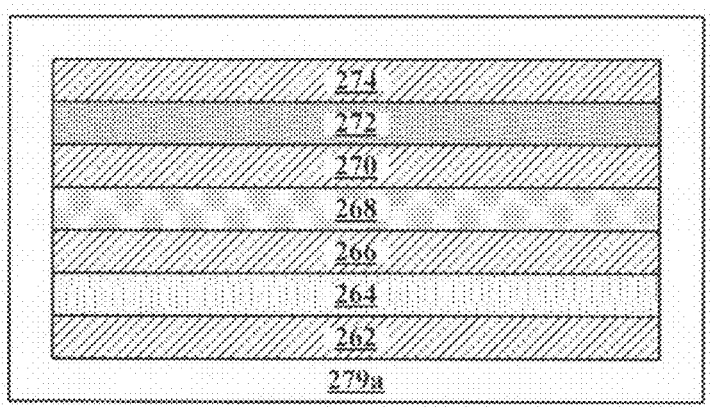
FIG. 2O depicts another preferred embodiment of a sensing apparatus of this invention.

Referring now to FIG. 2O, another preferred embodiment of a composite biosensor of this invention, generally 260, is shown to include a first LBL layer 262, a first responsive layer 264, a second LBL layer 266, a second responsive layer 268, a third LBL layer 270, a third responsive layer 272, and a fourth LBL layer 274 all surrounded or encased by a coating 279a. Again, each LBL layers can be the same or different and each responsive layers can be the same or different.

Figure 2P:
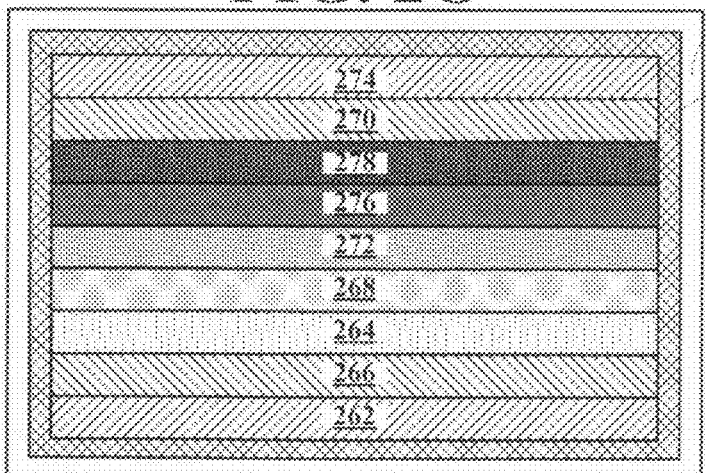
FIG. 2P depicts another preferred embodiment of a sensing apparatus of this invention.

Referring now to FIG. 2P, another preferred embodiment of a composite biosensor of this invention, generally 260, is shown to include a first LBL layer 262, a second LBL layer 266, a first responsive layer 264, a second responsive layer 268, a third responsive layer 272, a fourth responsive layer 276, a fifth responsive layer 278, a third LBL layer 270, and a fourth LBL layer 274 all surrounded by a mesh cover 279b, which is in turn surrounded or encased by a coating 279a.

Patterned Biosensors and Detection Systems

Figure 2Q:
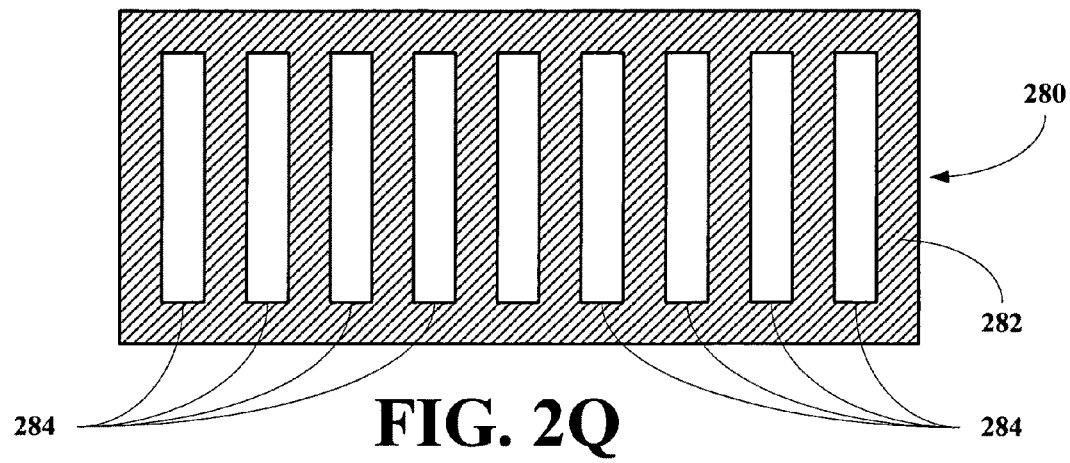
FIG. 2Q depicts a preferred embodiment of a patterned composite biosensor of this invention.

Referring now to FIG. 2Q, a preferred embodiment of a patterned composite biosensor of this invention, generally 280, is shown to include an LBL base layer 282 and a plurality of lateral responsive strips 284 formed on the LBL base layer 282. The strips 284 can be the same or different responsive material. The patterns can be formed on the base layer by any known patterning process including photoresist techniques, contact microprinting techniques or any other technique known that allows patterns to be formed on base layers. Once the strips 284 are formed a second LBL layer (not shown) can be formed on top encasing the strips 284.

Figure 2R:
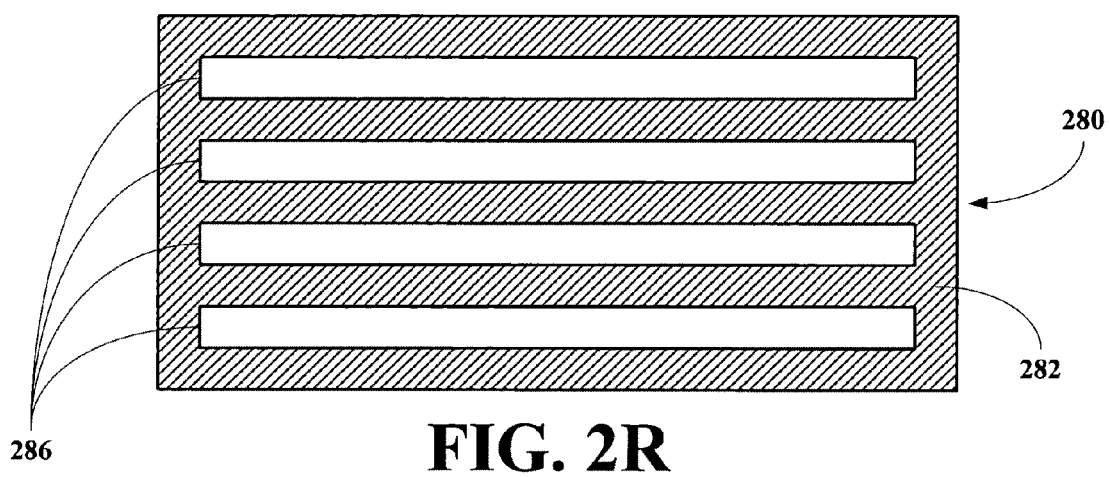
FIG. 2R depicts another preferred embodiment of a patterned composite biosensor of this invention.

Referring now to FIG. 2R, another preferred embodiment of a patterned composite biosensor of this invention, generally 280, is shown to include an LBL base layer 282 and a plurality of longitudinal responsive strips 286 formed on the LBL base layer 282. The strips 286 can be the same or different responsive material. The patterns can be formed on the base layer by any known patterning process including photoresist techniques, contact microprinting techniques or any other technique known that allows patterns to be formed on base layers. Once the strips 286 are formed a second LBL layer (not shown) can be formed on top encasing the strips 286.

Figure 2S:
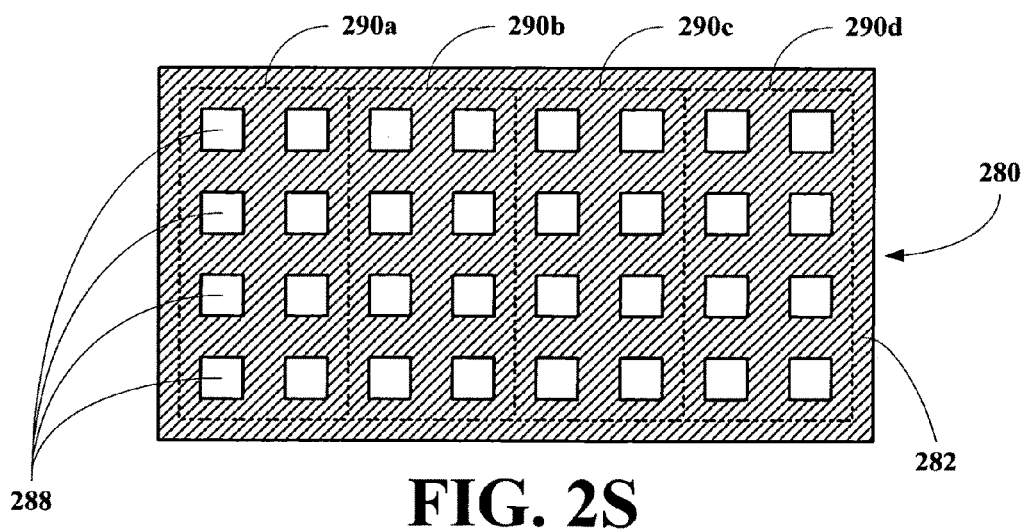
FIG. 2S depicts another preferred embodiment of a patterned composite biosensor of this invention.

Referring now to FIG. 2S, another preferred embodiment of a patterned composite biosensor of this invention, generally 280, is shown to include an LBL base layer 282 and a plurality of responsive patches 288 formed on the LBL base layer 282. The patches 286 can be the same or different responsive material and a preferably segmented into areas 290a-d; each area responsive to different biological agent such as a protein, antigen, immunoglobin, blood constituent, or bodily fluid constituent. The patterns can be formed on the base layer by any known patterning process including photoresist techniques, contact microprinting techniques or any other technique known that allows patterns to be formed on base layers. Once the strips 286 are formed a second LBL layer (not shown) can be formed on top encasing the strips 286.

Combined Biosensors and Detection Systems

The present invention also contemplates the implantation or placement of combined biosensor/detector apparatus, where the apparatus include an excitation or probing component, a biosensor and a detection component. Because the components are to be implanted or placed in contact with the biological system in a self-contained fashion, the apparatuses are designed to be either battery powered or more preferably field activated. Regardless of the source of power, the apparatuses are designed to monitor a desired property of a biological system without external excitation and detection systems. The excitation source generally is a photoemitting diode which generate an electromagnetic output. For example, if the biosensor is designed to monitor glucose concentration, the photoemitting diode preferably generates light in the near to mid infrared spectrum and the detector is a photosensor capable of detecting transmitted near to mid IR radiation and produce an absorbance spectrum. The detector system is also designed to transmit the spectrum to a receiver external to the biological system which then converts the transmission into a human readable form. If the biosensor undergoes a turbidity change or other change which is more readily detected from the reflectance spectra, then the detector system is capable of detecting a reflectance spectrum and transmitting the spectrum to the receiver.

Figure 3A:
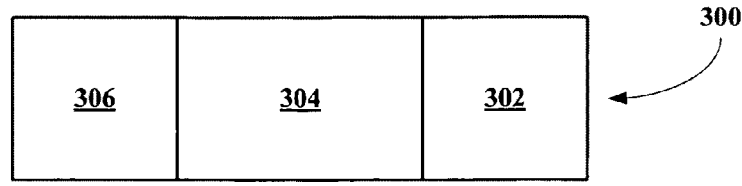
FIG. 3A depicts a preferred embodiment of a detecting apparatus of this invention.

Referring now to FIG. 3A, a preferred embodiment of a combined biosensor/detector of this invention, generally 300, is shown to include an electronic excitation component 302 adapted to produce an excitation or input waveform directed at a biosensor 304 adjacent thereto. Once the excitation or input waveforms passes through the biosensor 304 to produce a response or output waveform which enters an adjacent electronic detection component 306. Although the electronic excitation component 302 can be any electronic system capable to producing an excitation waveform, the electronic excitation component is preferably a field activated microelectronic component including circuitry for absorbing power from an imposed external field (generally, an RF field) and producing an excitation waveform, which can be optical via a photoemitting diode or sonic via a piezoelectric transducer or similar device capable of producing an acoustic waveform. Similarly, the electronic detection component 306 can be any electronic system capable of detecting an output waveform and converting the output waveform into a data stream for transmission to a receiving system external to the body. Preferably, as with the electronic excitation component 302, the electronic detection component is a field activated microelectronic component including circuitry for absorbing power from an imposed external field (generally, an RF field), receiving the output waveform (piezoelectric transducers, photosensitive transistors, etc.), converting the output waveform to a data stream and transmitting the data stream to a receiver external to the body or biological system.

Figure 3B:
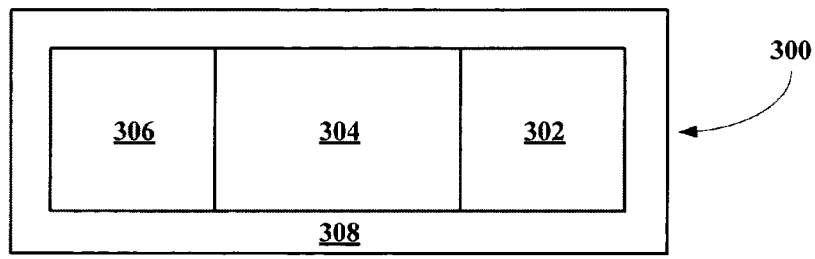
FIG. 3B depicts another preferred embodiment of a detecting apparatus of this invention.

Referring now to FIG. 3B, another preferred embodiment of a combined biosensor/detector of this invention, generally 300, is shown to include an electronic excitation component 302, a biosensor 304, and an electronic detection component 306 all surrounded by or encased in a coating 308. As described above, the electronic excitation component 302 produces an input waveform that travel through the biosensor 304 to produce an output waveform that enters the electronic detection component 306, where it is received, converted to a data stream and transmitted away from the biosensor/detector, i.e., to a receiver external to the body or biological system. Again, the electronic components 302 and 306 are as described above.

Figure 3C:
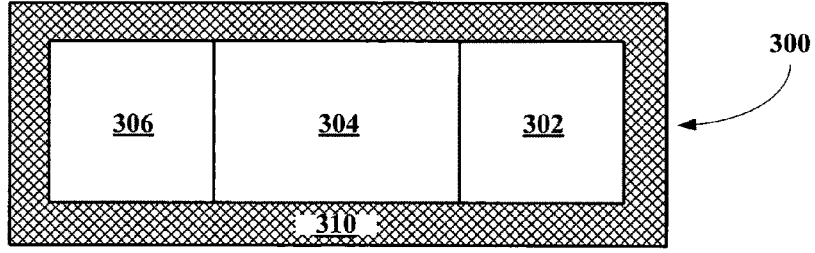
FIG. 3C depicts another preferred embodiment of a detecting apparatus of this invention.

Referring now to FIG. 3C, another preferred embodiment of a combined biosensor/detector of this invention, generally 300, is shown to include an electronic excitation component 302, a biosensor 304, and an electronic detection component 306 all surrounded by or encased in a mesh 310. As described above, the electronic excitation component 302 produces an input waveform that travel through the biosensor 304 to produce an output waveform that enters the electronic detection component 306, where it is received, converted to a data stream and transmitted away from the biosensor/detector, i.e., to a receiver external to the body or biological system. Again, the electronic components 302 and 306 are as described above.

Figure 3D:
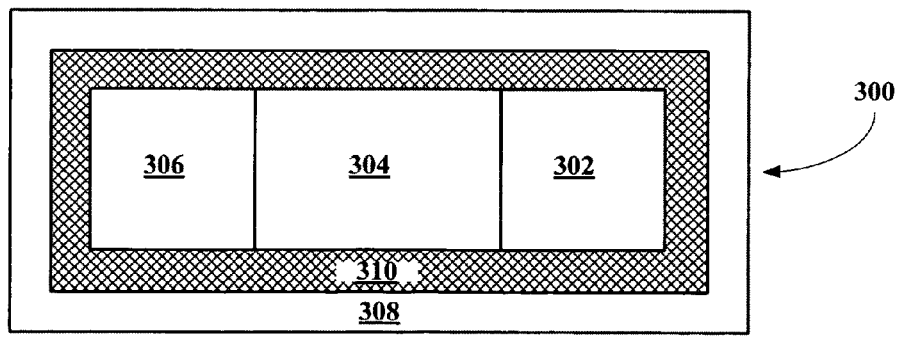
FIG. 3D depicts another preferred embodiment of a detecting apparatus of this invention.

Referring now to FIG. 3D, another preferred embodiment of a combined biosensor/detector of this invention, generally 300, is shown to include an electronic excitation component 302, a biosensor 304, and an electronic detection component 306 all surrounded by a mesh 310 which is in turn surrounded by or encased in a coating 308. As described above, the electronic excitation component 302 produces an input waveform that travel through the biosensor 304 to produce an output waveform that enters the electronic detection component 306, where it is received, converted to a data stream and transmitted away from the biosensor/detector, i.e., to a receiver external to the body or biological system. Again, the electronic components 302 and 306 are as described above.

Detection Apparatuses Incorporating a Biosensor or a Biosensor/Detector

Referring now to FIGS. 4A&B, a preferred embodiment of a detection/analysis systems using the biosensors of FIGS. 2A-P, generally 400, are shown. Looking at FIG. 4A, the system 400 includes a biosensor 402 implanted in a tissue 404, an excitation source 406 adapted to produce an input or excitation waveform 408. The input waveform 408 impinges on the biosensor 402 resulting in a reflected or output waveform 410 which is received by a detector/analyzer 412. Although the system is shown here in a reflectance mode, the detector/analyzer 412 can also be positioned opposed the excitation source 406 thereby receiving a transmission waveform. Moreover, two detector/analyzers 412 can be used, one as shown and one positioned opposite the excitation source 406 so that both a reflectance and transmission waveform can be received and analyzed. The detector/analyzer 412 receives and processes the output waveform in to a curve or numeric value representing a value of the property being monitored.

Looking at FIG. 4B, the system 400 includes a biosensor 402 in contact with a tissue 404. Again, the system 400 also includes an excitation source 414 adapted to produce an input or excitation waveform 408. The input waveform 408 impinges on the biosensor 402 resulting in a reflected or output waveform 410 which is received by a detector/analyzer 412. Although the system is shown here in a reflectance mode, the detector/analyzer 412 can also be positioned opposed the excitation source 406 thereby receiving a transmission waveform. Moreover, two detector/analyzers 412 can be used, one as shown and one positioned opposite the excitation source 406 so that both a reflectance and transmission waveform can be received and analyzed. The detector/analyzer 412 receives and processes the output waveform in to a curve or numeric value representing a value of the property being monitored.

Referring now to FIGS. 4C&D, another preferred embodiment of a detection/analysis systems using the biosensor/detectors of FIGS. 3A-D, generally 450, are shown. Looking at FIG. 4C, the system 450 includes a biosensor/detector 452 comprising an electronic excitation component 454 adapted to produce an excitation or input waveform directed at a biosensor 456 adjacent thereto. As the excitation or input waveform passes through the biosensor 456 it interacts with the biosensor 456 to produce a response or output waveform which enters an adjacent electronic detection component 458. The biosensor/detector 452 is shown implanted in a tissue 460. The system 450 also includes a field generator/analyzer 462 adapted to generate a field 464 to supply power to the excitation component 454 and the detector component 458, to receive transmissions 466 from the electronic detection component 458 in the form of an electromagnetic or sonic transmission and to convert the transmitted data into a measure of the property being monitored. Although the biosensor/detector 452 is configured for detection of a transmission waveform, the excitation component 454 can also include a detection and transmission circuitry for detection and transmission of data associated with a reflected waveform.

Looking at FIG. 4D, the system 450 includes a biosensor/detector 452 comprising an electronic excitation component 454 adapted to produce an excitation or input waveform directed at a biosensor 456 adjacent thereto. As the excitation or input waveform passes through the biosensor 456, it interacts with the biosensor 456 to produce a response or output waveform which enters an adjacent electronic detection component 458. The biosensor/detector 452 is shown in contact with a tissue 460. The system 450 also includes a field generator/analyzer 462 adapted to generate a field 464 to supply power to the excitation component 454 and the detector component 458, to receive transmissions 466 from the electronic detection component 458 in the form of an electromagnetic or sonic transmission and to convert the transmitted data into a measure of the property being monitored. Although the biosensor/detector 452 is configured for detection of a transmission waveform, the excitation component 454 can also include a detection and transmission circuitry for detection and transmission of data associated with a reflected waveform.

The universality of the stratified membrane approach affords inclusion of many functional features into the biosensor of this invention. For example, the central layer can serve as a sensing layer. In this case, appropriate materials for each outer layer and the central layer will be chosen so that the change in morphological (i.e., shape thickness, etc.), biochemical/biophysical, optical, spectroscopic, acoustic, electrical, magnetic and mechanical properties of the sensing layers can be monitored or imaged continuously or quantified using steady state, time resolved or ratiometric measurement technique.

The central layer and/or the outer layer can also contain the supporting compounds and function as bioreactor to prolong the in-vivo functioning of the sensor and/or improve its performance. One of the implementations of this function is incorporation of biological or chemical catalysts such as enzymes or metal complexes for decomposition of hydrogen peroxide into dioxygen and water. The molecule of hydrogen peroxide are generated when glucose peroxidase reacts with glucose, which serves as the common reaction for many glucose sensors. This reaction produces hydrogen peroxide and consumes oxygen. Most of the current glucose sensors monitor its concentration either by oxygen consumption or by peroxide concentration; both of these schematics are possible for the proposed stratified membrane. At the same time, for an implantable sensor, the availability of oxygen for glucose oxidation may become difficult due to limited oxygen supply in the tissue. In this case the incorporation of the catalyst that can partially regenerate hydrogen peroxide into oxygen will be significant for its proper functioning.

When central layer serve as a sensor layer the internal reference signal will be provided by an identical stratified membrane without biosensitive materials implanted near the sensing one or by incorporation of reference points in the sensing element with constant physical or chemical properties.

One of the surfaces and interfaces of the implantable sensor can be modulated to effect diffraction of electromagnetic radiation. The change of the spatial modulation effected by the analyte will report its presence and concentration. Both intensity and the wavelength alterations of the diffracted light can be used for analyte reporting.

The outer layer(s) can also serve as sensing layer(s). In this case, the biosensing molecules are placed in the one of outer layers or at its interface with the central layer. The other outer layer will be devoid of the biosensing compounds and will act as a reference and internal calibration.

The multilayer sensor can also be produced as spatially patterned sheets with different patterned elements as shown in FIGS. 2A-S. Patterned sensing elements can be arranged in specific areas of the membrane biosensor to response to specific biological system characteristics where functionality was imparted to the biosensor during the assembly procedure. Some of them can be assembled to be sensing elements and some of them can be sensing elements, which will be separated by nonactive parts of the membranes. Every patterned elements can be assembled from a different layer sequence. The patterning of the multilayer sheets can also be realized to produce implantable devices for an array of different analytes with corresponding internal calibration spatial units.

Selective rejection, retention or uptake of specific biological molecules by developing membrane strata that facilitate selective transport of desired molecule(s) mediated by morphological and/or biochemical properties of the membrane. For example, glucose specific receptor can be assembled within the stratified membrane in order to improve the specificity of the sensor. Another approach would be to use NPs, nanoshells, nanosheets, or other colloids as molecular sieves to ensure the passage of molecules with predetermined size.

The membrane can be implanted percutaneously, intraocular or into other organs. The deep tissue localization of the membrane is also possible as permitted by the remote sensing capabilities of the selected spectroscopic and/or imaging technique.

The stratified membrane sensor can be used for both long-term months-years) and transient (hours-days) monitoring of body parameters relevant for a specific human/animal activity.

The so-called layer-by-layer deposition process/method (LBL) can be used to form films composed of alternating layers of magnetite nanoparticles and poly(diallyldimethylammonium bromide) assembled on cellulose acetate, a removable substrate; the details of which is set forth in Langmuir 2000, 16 5530-5533, incorporated herein by reference.

One preferred dissolvable substrate is cellulose acetate. The preferred process involves supporting the cellulose acetate on a glass slide to improve lift-off of the LBL assembly after formation. The glass surface is thoroughly cleaned in hot $H_2O_2/H_2SO_4$ (1:3) mixture for 5 min. Subsequent to thorough washing and drying, a few drops of 15% solution of cellulose acetate in acetone were cast on the slide and allowed to spread forming a thin uniform coating. Immediately after that, the slide was placed in a dessicator and the solvent was allowed to slowly evaporate. When the film solidified, the traces of acetone were completely removed in vacuum.

The LBL assembly can then be carried out by a cyclic repetition of the following operations: (1) dipping of the cellulose acetate-coated slide in 1% aqueous solution of poly (dimethyldiallylammonium bromide) 400-500 kDa, P, for 1 min, (2) rinsing with deionized water for 1 min; (3) dipping in a solution of negatively charged colloid for 1 min; and (4) rinsing with water. Many colloidal solutions can be used including, without limitation, colloidal solutions of negatively-charged particles such as 8-10 nm magnetite nanoparticles, other magnetically active nanoparticles, silica nanoparticles, alumina nanoparticles, titania nanoparticles, other oxide nanoparticles, carbon nanotubes, silicon nanotubes, semiconductor nanoparticles, buckminsterfullerenes, quantum dots, metallic clusters, or any other molecular or assembly of atom nanoparticles, where the term nanoparticle means that the particle size is less than or equal to 1 micron.

Optical Coherence Tomography

Optical coherence tomography (OCT) is a newly developed high-resolution imaging technique. The method uses an interferometer, in which light in one arm is aimed into the tissue to be imaged. Light that is coherently backscattered from structures within the tissue (up to a few mm) is collected and interfered with the light from the reference arm, allowing a measurement of the echo time delay and in amplitude of the reflected light. The method uses a light source with low coherence and uses correlation to measure the delay, i.e., the depth of the backscattering features. By gathering interference data at points across the surface, cross-section images can be formed effectively in real time with resolution of about 5 to about 10 μm.[2,4]

The inventors were to report the application of OCT for sensing and monitoring of glucose.[1,3,4] The technique offers three distinct advantages over conventional optical monitoring techniques. First, OCT provides the capability to resolve tissue structure with high resolution (~10 μm) and the most accurate way to measure changes in optical properties within a pre-determined region of tissue in vivo. Second, the use of a low coherence light source provides a unique opportunity to detect ballistic photons and thus accurately measure glucose-induced changes in backscattering properties of cells in tissue. Third, OCT can resolve the wavelength dependence of optical pathlength in tissue on glucose concentration with a high degree of sensitivity.

Another novel aspect of this invention is the use of thin film made up of nanoparticles (NP) to enhance optical contrast and chemical specificity of an implant designed to monitor a specific biomolecule such as glucose sensing.

For imparting biocompatibility, the biosensors or biosensor/detectors can be surrounded, encased or embedded in a biocompatible material or mixtures of biocompatible materials including, without limitation, polyurethanes such as BioSpan®, Bionate®, Elasthane™, PurSil™ and CarboSil™ available from The Polymer Technology Group, Acrylate polymers and copolymers: methyl methacrylate, methacrylic acid, hydroxyalkyl acrylates and methacrylates, ethylene glycol dimethacrylate, acrylamide, bisacrylamide, Cellulose-based polymers, Ethylene glycol polymers and copolymers, Oxyethylene and oxypropylene polymers, Poly(vinyl alcohol) and Polyvinylacetate, Polyvinylpyrrolidone and polyvinylpyridine or the like. Besides biocompatible polymers, biocompatible, bio-degradable polymers can also be used including, without limitation, Polylactide (PLA), Polyglycolide (PGA), Lactide-glycolide copolymers (PLG), Polycaprolactone, Lactidecaprolactone copolymers, Polyhydroxybutyrate, Polyalkylcyanoacrylates, Polyanhydrides, Polyorthoesters, Proteins: albumin, collagen, gelatin, Polysaccharides: dextrans, starches, or the like. Additional biocompatible biodegradable polymers can be found in U.S. Pat. Nos. 5,607,474; 5,876,452; 6,187,329; and 6,255,359, incorporated herein by reference.

Experimental Section

To demonstrate the capability of OCT to monitor glucose-induced changes in the optical properties of tissue (i.e., optical pathlength) in vivo, experiments were conducted using an OCT system operating at 1300 nm with output power of about 0.5 mW. Two-dimensional intensity distributions from each image were averaged into a single curve to obtain 1-D distribution of light in depth. The 1-D distributions were plotted in logarithmic scale as a function of depth for further analysis. The average slopes (5 images) of obtained OCT signals were calculated and plotted as a function of time or as a function of blood glucose concentration.

Bolus glucose injection and glucose clamping experiments were performed in 4 hairless Yucatan micropigs (best model for human skin) and 6 New Zealand rabbits. OCT images were taken from the dorsal area (micropigs) or inner area of the right ear or the eye of rabbit while the probe was in contact. Blood glucose concentration was monitored with a Beckman glucose analyzer.

Figure 10A:
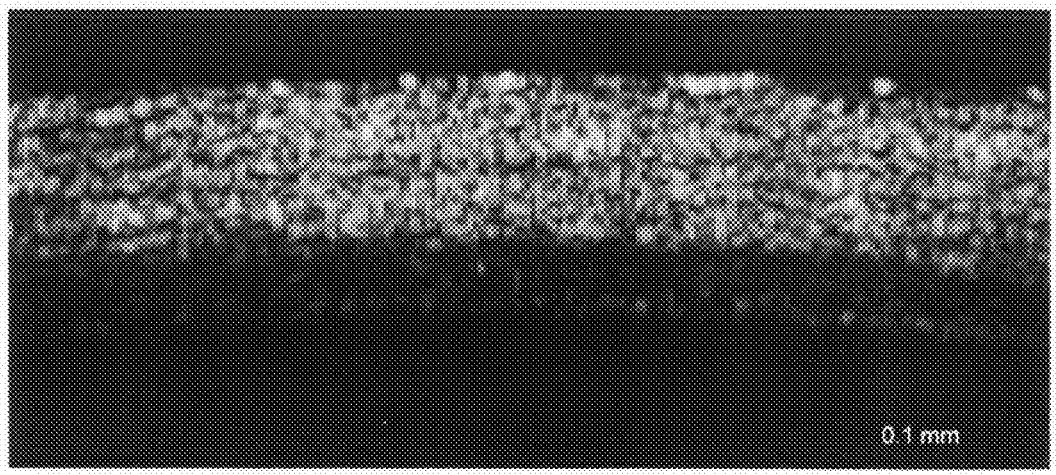
Figure 10B:
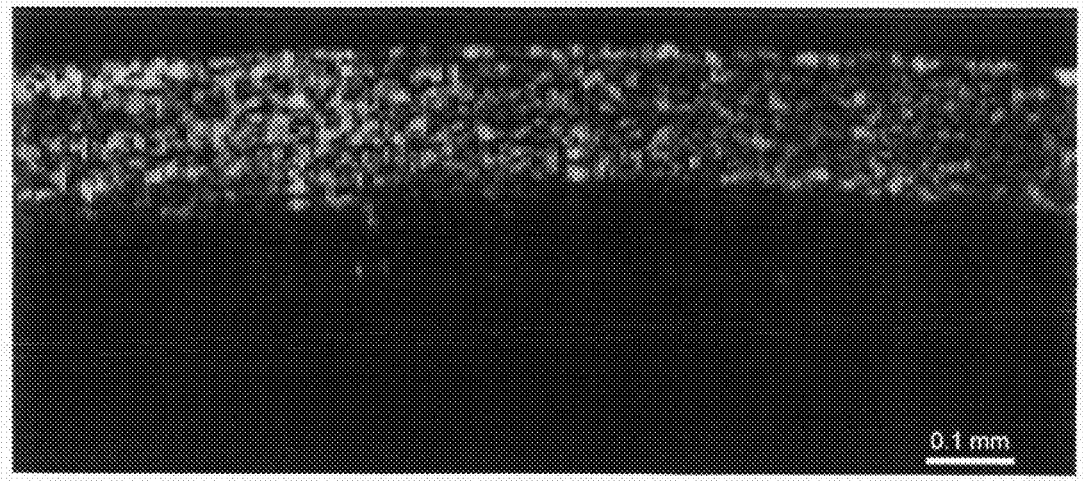
Figure 11:
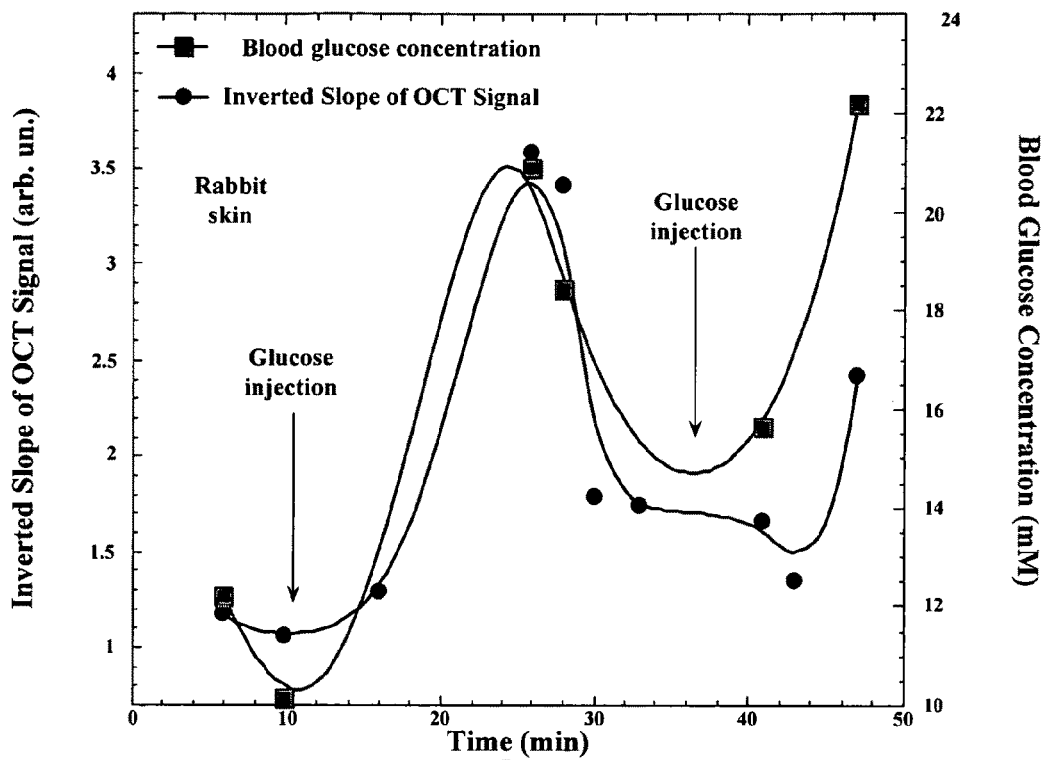
FIG. 11 depicts inverted slope of OCT signals (recorded from rabbit ear) and blood glucose concentration measured at different time during bolus glucose injections.
Figure 13:
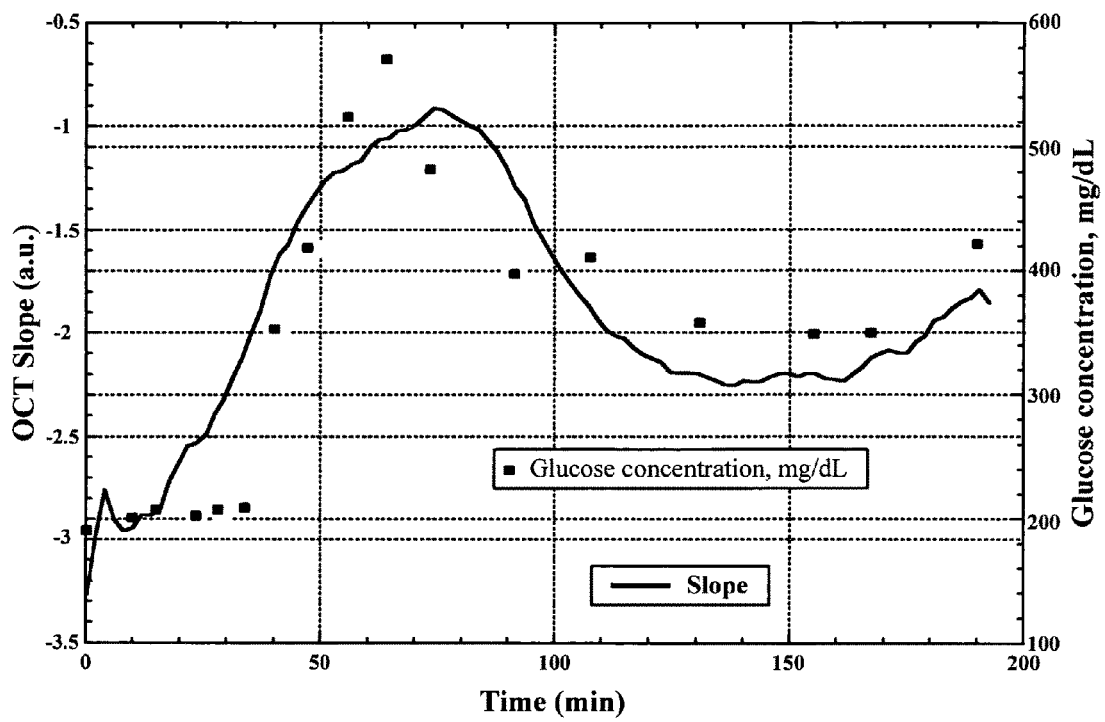
FIG. 13 depicts Slope of in-vivo OCT signal (recorded from sclera of rabbit eye) and blood glucose concentration as a function of time during glucose clamping experiment.

Referring now to FIG. 13, show the influence of glucose on light scattering in sclera of rabbit eye as function of glucose concentration. Notice the sharp difference between the optical contrast (bright region) within the tissue in FIG. 10A (10 mM) vs. that in FIG. 10A (29 mM) demonstrating how significantly light scattering in tissue (i.e., optical pathlength) is affected by changing blood glucose. Inverted slope of the OCT signal recorded from the Rabbit ear and corresponding blood glucose concentrations measured at different time during the bolus injection experiment are shown in FIG. 11. Slope of OCT signals were measured at the depth from about 150 to about 200 µm. Good correlations between actual blood glucose concentration and inverted slope of OCT signal is demonstrated.

Figure 12:
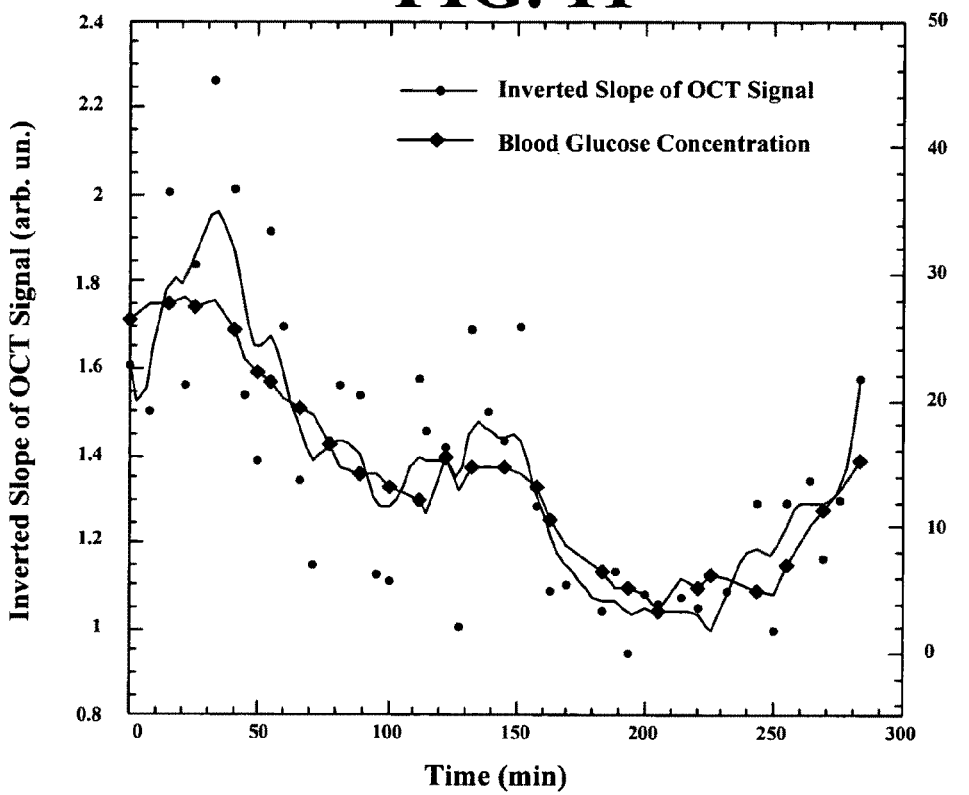
FIG. 12 depicts Inverted slope of OCT signals (recorded from Yucatan pig skin) and blood glucose concentration measured at different time during glucose clamping experiments.

In another study, glucose clamping experiments were performed to demonstrate that the changes of OCT slope were not induced by bolus glucose injections. Referring now to FIG. 12, the data demonstrate that the inverted slope of the OCT signal obtained from skin tissue followed blood glucose concentration during glucose clamping experiments in Yucatan micropigs. The correlation is substantially better after about 1.5 to about 2.5 hrs. following induction of epidural anesthesia and subsequent stabilization of fluid transport and shifting in skin. In the sclera of rabbit eye as shown in FIG. 11, the OCT signal is tracking the changes in blood glucose very closely over the entire period of the experiment. This is most likely related to the fact that the amount of fluid shifting following induction of anesthesia is significantly less in the sclera as compared to skin tissue.

Figure 14:
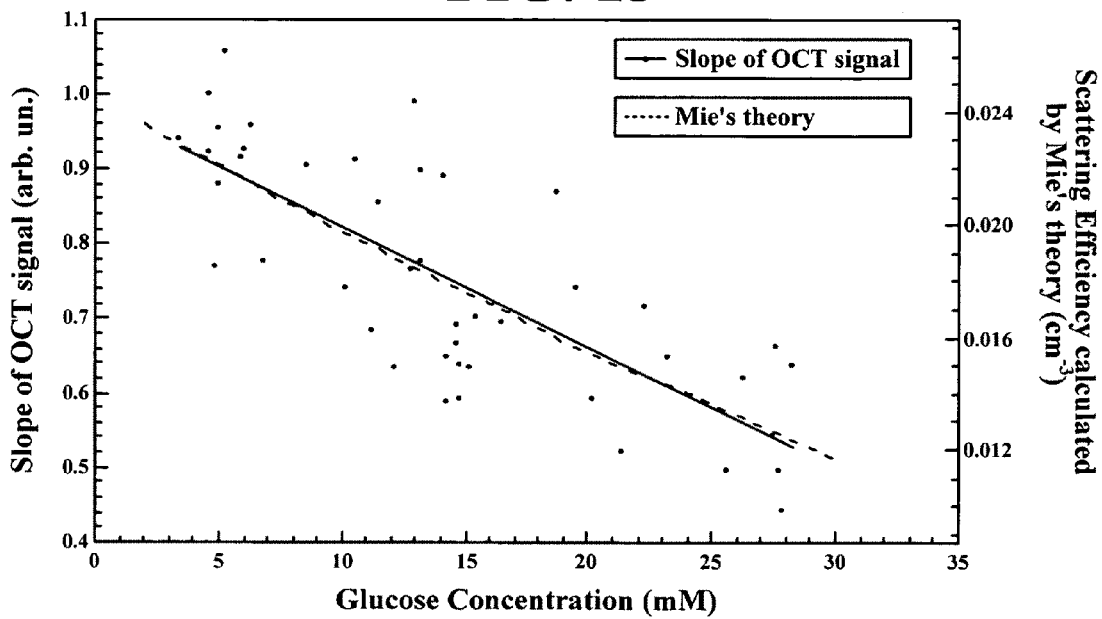
FIG. 14 depicts Slope of OCT signals (recorded from Yucatan pig skin) measured during glucose clamping experiments as a function of blood glucose concentration and scattering efficiency calculated by Mie's theory.

Other factors could be the differences in the optical properties of skin vs. sclera. The results demonstrate that the slope of OCT signal decreases substantially (about 40.5%) and linearly with the increase of blood glucose concentration from 4 to 28.5 mM (physiologic range typical for normal and diabetic subjects). Theoretical calculations performed on the basis of Mie's scattering by long cylinders (assuming, index of refraction of 1.360 for cell membranes, 1.357 for interstitial fluid, and diameter of 15 µm for scatterers), the calculations reveal good correlation with experiments. FIG. 14 shows the slope of OCT signals (recorded from Yucatan pig skin) as function of blood glucose concentration and scattering efficiency calculated by Mie's theory. The study supports our hypothesis that the changes in the OCT slope are produced by changes in the scattering coefficient of tissue.

Research Design & Methods

Figure 5:
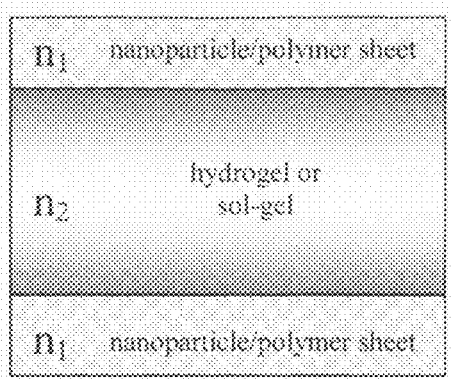
FIG. 5 depicts a schematic of proposed nano-structure sensor.
Figure 6:
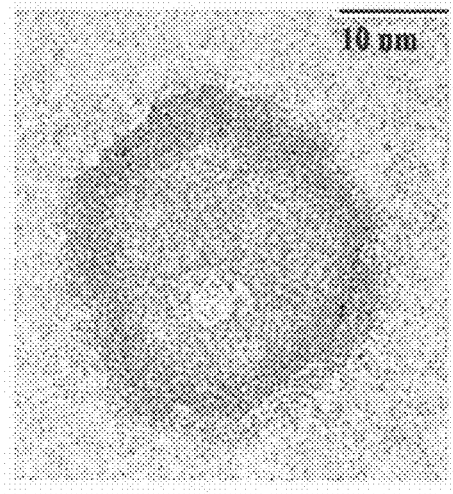
FIG. 6 depicts a transmission electron microscopy image of $TiO_2$ nanoshells.
Figure 7:
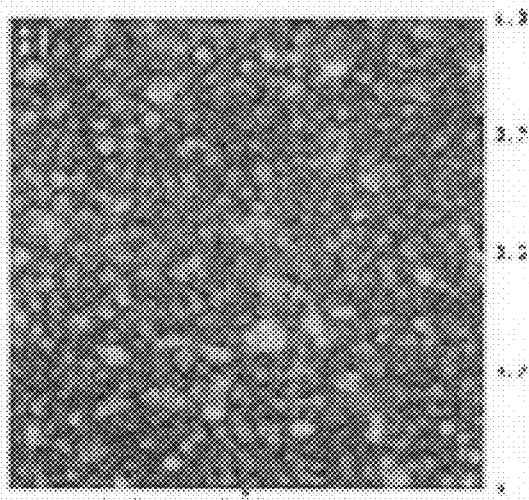
FIG. 7 depicts an AFM image of LBL films of $TiO_2$ nanoshells.
Figure 8A:
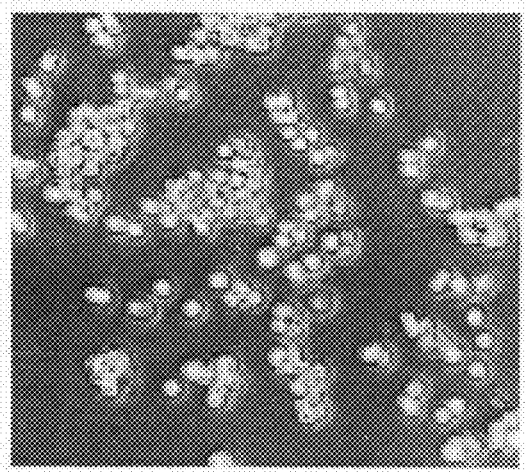
FIG. 8 depicts PC12 pheochromocytoma cells (left) and C2C12 myoblast cells attached to the NP LBL films.
Figure 8B:
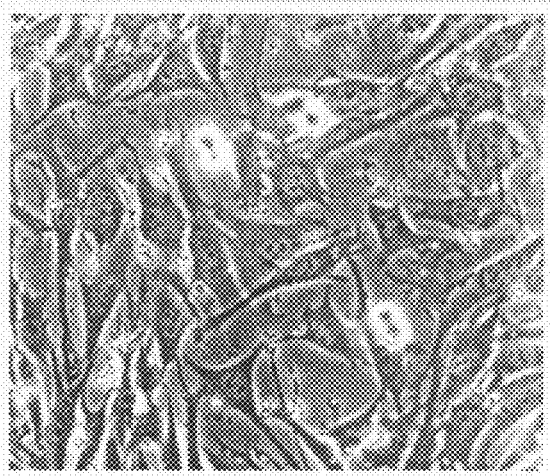

By taking advantage of recent developments in nanoparticles and thin film technology, micro-optics, and polymer technology, a multilayer, implantable, sensor is presented that is capable of monitoring at least one characteristic or property of a biological system. For example, a responsive layer such as a hydrogel or sol-gel material layer that undergoes a physical (size) and/or chemical (turbidity) change in response to changes in glucose concentration sandwiched between two outer layers of a biocompatible polymer that readily allows for the transport of glucose into the responsive layer as shown in FIG. 5 makes an effective glucose sensor of this invention. The sensing element hydrogel changes thickness[7,4] or index of refraction[8,4] as function of glucose concentration. Sol-gel represent the other sensing element because such materials undergo a change turbidity (i.e., scattering) as function of glucose concentration.[10,4] To create an optical contrast between the outer layers of the sensor and the surrounding tissue, the outer layers are fabricated using the LBL assembly technique described earlier including hollow titanium dioxide (highly biocompatible) shells with a diameter of 100-200 nm as shown in FIG. 6 as nanoparticles to enhance the optical contrast between the sensor and the tissue surrounding it. The contrast is due to a large difference between the index of refraction of tissue (~1.3-1.4) and that of TiO2 (2.2-2.4). The LBL sheet of the nanoshells form well packed films as shown in FIG. 7, but still possess sufficient number of pores to be permeable to small molecules like glucose as was recently demonstrated for a neurotransmitter dopamine transport.[23,4] Importantly, these films were also demonstrated to be biocompatible. They support, attachment, growth, and development of C2C12 myoblast and PC12 pheochromocytoma cells as shown in FIG. 8.

Figure 9:
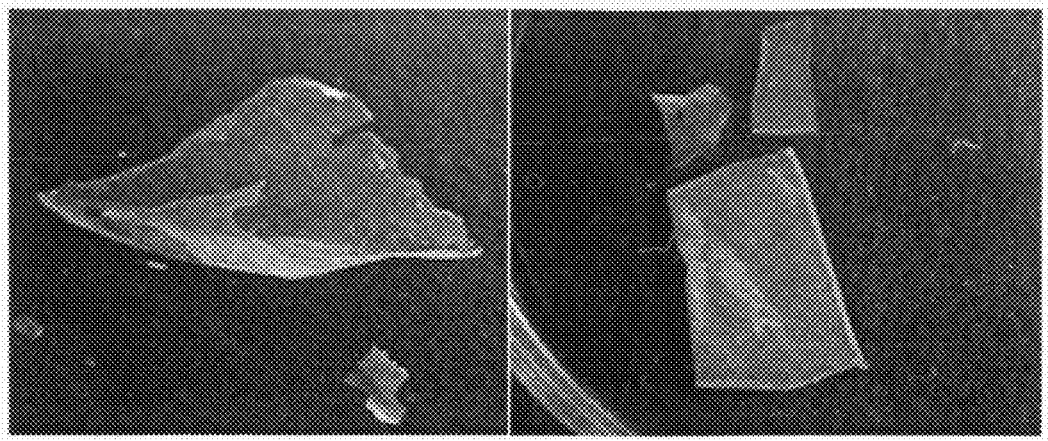
FIG. 9 depicts a free-standing LBL films of CdTe nanoparticles of different diameters: 2.5 nm CdTe (left) and 5.3 nm CdTe (right), FIGS. 10A&B depicts in-vivo OCT images of rabbit sclera as a function of glucose concentration.

The layer containing nanoparticles is first assembled on a suitable substrate to produce a layer 0.3-1 µm thick. Then the middle layer will be deposited using hydrogel or sol-gel that will be prepared using well established preparation formula that are known to react with glucose and change morphological and/or optical properties.[7A,8A,10A] The deposition of the gel on the first layer containing nanoparticles can be achieved by using spin coating technique. The thickness of this layer can be made up to 1 mm. Then, this two-layered structure will be covered by another layer of LBL developed sheet of nanoparticles. The outer LBL nanoparticle coatings serves as a transport layer, which permits glucose easy access to the inner hydrogel or sol-gel layer. In addition, both nanoparticle films will exhibit strong optical scattering, and therefore will be highly visible in OCT. The increase or decrease in glucose concentration causes expansion/contraction or refraction of light within the hydrogel layer and alters the separation between the two outer layers, or light distribution, within the sensor which can be monitored on the OCT image. For the case in which sol-gel is used as the sensing element, the change in glucose concentration alters the turbidity of this layer which can be accurately quantified using OCT/interferometric measurements. This technique for making films of this invention allow for ready optimization of the thickness of both outer layers and selection of material that form the center layer (hydrogel or sol-gel). Recently, the first examples of self-sustained LBL films were made FIG. 9.[24A] Such films are particularly attractive as sensor implants because they minimize possible damage to the tissues surrounding an implant while providing additional strength for the implant.

Sensor specificity for glucose detection could be further improved by designing the outer layers with porous material that can be fabricated to ensure selective passage of molecules that are the same size as glucose. To increase a specificity of the sensor, enzymatic layers can be included in the construction. For example, glucose oxidase (GOx) converts glucose in the presence of $O_2$ to D-gluconolactone and $H_2O_2$. D-gluconolactone will shift pH to lower values which induces the polymer shrinkage or changes in optical properties of gel that can be monitored by OCT. To deplete $H_2O_2$, a conjugated layer of catalase (Cat) is included, which coverts $H_2O_2$ to $O_2$. Therefore, using the layer-by-layer assembly of organized multi layers by alternate adsorption of oppositely charged enzymes (GOx and Cat) and polyions will introduce these enzymes into the inner part of the $TiO_2$ layers if needed. GOx and catalase multi layers assembly demonstrate that GOx being immobilized with polyions has enhanced activity properties. In the multilayer with polyethyleneimine it preserved 90% of activity for 3 month, while GOx in solution retained only 15% of its activity after this time. The variables of sensor optimization include OCT/interferometric detection, biosensor dimension and structure which evidence glucose-induced alteration in the optical (i.e., turbidity, color, index of refraction) or geometrical properties (i.e., thickness) of the inner layer of the sensor as function of glucose concentration.

Stratified Biocompatible Films Semiconductor Nanoparticles and Collagen

Polymer/inorganic nanocomposites hold much promise for the production of novel materials, in which optical, electrical, magnetic, and catalytic properties of inorganic nanostructures are combined with optical, electrical, and mechanical properties of macromolecules. The mosaic of chemical and physical characteristics available for permutations from both classes of compounds provides a versatile platform for materials designed for different purposes. Numerous pilot devices and unique materials with primary applications in advanced optical, electrical, chemical and mechanical engineering have been demonstrated.[1A] A large class of very demanding applications, where the adaptability of polymer/inorganic nanocomposites could be particularly valuable is biomaterials. Interestingly, the use of nanoparticle-polymer composites for this purpose has received relatively little attention so far and represents an interdisciplinary field of science with much research work still to be done. One of the most high-impact applications in this area are biomedical sensors,[2B-4B] for which the quantum confinement effects observed in nanoparticles (NPs) can be a vast resource for the improvement of current biomedical technologies.

In many ways, biosensors serve as an interface between live and electronic organisms, and therefore, should meet rigid requirements that satisfy both worlds. The presence of a foreign object inside of living tissue is intrinsically hazardous. So, one of the key requirements to biosensors is biocompatibility.[5B] In fact, this should be considered as the starting point for the design and fabrication of any implantable devices or devices in contact with a body part such as a mucosal membrane, the surface of the eye, the skin or the like. Harmonious coexistence of live and man-made matter normally requires a buffer zone with properties tailored to both sides. This implies the necessity of a structural and functional gradient in the buffer zone. The nanoparticle/polymer composites with controlled stratification and property gradient were recently made by layer-by-layer assembly (LBL).[6B-8B] This technique is very convenient for this purpose because (1) films can be constructed as layered stack utilizing both inorganic NPs and biomolecules and (2) the composition of the films can be easily changed from layer to layer in accord with the desired evolution of properties or end result.

EXAMPLES

Chemicals

All the chemicals, unless otherwise specified, were purchased from Aldrich (Milwaukee, Wis.) and were used without further purification. Collagen type IV (acid soluble, from human placenta) was purchased from Sigma-Aldrich (St. Lois, Mo.). Ultrapure 18 MΩ/cm water was used for all experiments and for washing. The pH of solutions was adjusted with diluted HCl or NaOH. All experiments were performed under atmospheric conditions, except synthesis of semiconductor nanocrystals.

Procedures

Aqueous colloidal solutions of thioglycerol-capped CdTe nanocrystals were prepared as described previously.[9B] Before the assembly, the substrates were subjected to an extensive cleaning procedure. Glass and silica wafers were cleaned in freshly prepared "piranha" solution (2:1 concentrated 98% $H_2SO_4$: 30% $H_2O_2$, DANGEROUS in contact with organic matter) for 5 min then rinsed extensively with water, and finally dried under a stream of nitrogen. Petri dishes were used as received.

The LBL assembly was started with absorption of positively charged poly(dimethyldiallylammonium) chloride (PDDA), Mw=400,000-500,000 on a glass, silicon or plastic substrates, which are negatively charged due to the existence of native thin oxide layer on the surface. The sequence of operations resulting in the production of semiconductor NP films was the following: 1) dipping of the substrate into a solution of PDDA (0.5%, pH=3) for 10 minutes, 2) rinsing with water for 1 minute; 3) dipping into the dispersion of CdTe nanocrystals for 20 minutes; 4) rinsing with water again for 1 minute. On each exposed surface, such a procedure resulted in a "bilayer" consisting of a polymer/NP composite. The cycle can be repeated as many times as necessary to obtain a multilayer film of desirable thickness.

The biocompatible coating of collagen on the surface of assembled LBL film of NPs was built in the same cyclic manner. After a 1 min wash of the substrate in deionized water, the CdTe multilayer film with PDDA-primed surface was dipped into a 0.5 wt % solution of poly(acrylic acid), Mw=400,000-500,000 (PAA) at pH 4, which changes the surface charge to negative. Following the same washing procedure, the substrate was exposed to positively charged 0.1% solution of collagen type IV at pH 4 for 20 min and rinsed with water again. The further growth of PAA/collagen bilayers was accomplished by the repetition of the same cycle of immersion into the solution of PAA, rinsing, immersion into the collagen solution, and rinsing. This procedure results in the deposition of a film with a layer sequence of (PDDA/CdTe/)$_n$PDDA(/PAA/collagen)$_m$, where n and m are the number of the corresponding deposition cycles. After the final assembly cycle, the substrate was dried with a stream of nitrogen.

For cell culture studies, the films were deposited on a bottom of a Petri dish, which served as the LBL substrate. In this case, the polyelectrolyte, semiconductor nanocrystals, and collagen solutions and water for rinsing were poured into the Petri dish and remained there for the specified length of time.

Muscle myoblast cells (C2C12) were purchased from American Type Culture Collection (ATCC, Manassas, Va.). C2C12 cells were cultured in Dulbecco's Modified Eagle's medium (DMEM) containing 15% fetal bovine serum (FBS, Hyclone), 2% streptomycin/penicillin. The cells were removed from culture substrates with a brief trypsin/EDTA treatment and centrifuged. Before seeding, polystyrene Petri dishes with deposited LBL layers were sterilized with ethanol and air-dried in a sterile hood. C2C12 cells suspended in fresh medium were seeded on the substrates and allowed to adhere for 1 day in a 37° C. 5% $CO_2$/air 95% environment for 24 h (incubator, NuAir Inc., Plymouth, Minn.).

Instrumentation

Surface imaging of nanoparticles layers was performed by Nanoscope III (Digital Instruments/Veeco, Santa Barbara, Calif.). Atomic force microscopy (AFM) images were obtained in tapping mode with standard Si/N tips.

Ellipsometric measurements were made with an AutoEL MS ellipsometer from Rudolph Research Corp. (Flanders, N.J.). The measurements were performed using a 632.8 nm line of He/Ne laser incident upon the sample at 70°. The DafIBM program supplied by Rudolph Technologies was employed to determine film thickness.

UV-vis spectra were taken using a HP8453A diode array Hewlett-Packard spectrophotometer.

Attached cells were imaged using a Microflex UFX-DX inverted microscope (Nikon USA, Melville, USA) with 100× and 200× magnification.

Results and Discussion

In the biomedical field, LBL assembly is actively being utilized for production of micro- and nanocapsules for drug delivery,[10B] although the issues related to the actual contact of polyelectrolyte capsules with tissues and immune response to them have not been investigated yet. The first studies of solid LBL biomaterials considering the direct contact of multilayers and living cells appeared only recently.[11B-18B] Most of these works were concerned with polyelectrolyte-polyelectrolyte multilayers. Two other studies involve particles of calcium phosphate[12B] and titanium dioxide nanoshells.[14B] Notably, both parent materials are known for their intrinsically high biocompatibility, which significantly simplifies the problem. They also lack some important properties such as luminescence or magnetism, which makes it necessary to impart biocompatibility to NPs from more challenging materials, such as II-VI semiconductors.

Preparation and Structure

The LBL deposition of semiconductor CdTe NPs with PDDA as a partner polyelectrolyte was described in several previous publications, where the details about the CdTe multilayer build-up can be found.[8B,19B,20B] The structure of these films can be visualized by atomic force microscopy in a single (PDDA/CdTe), bilayer as shown FIG. 15. The NPs are closely packed forming a uniform coating of the substrate; the average height of surface features is ~1.5 nm.

Importantly, the films reveal strong luminescence with a quantum yield of 16% after the deposition (FIG. 16, trace 1). The wavelength of the luminescence is 620 nm, which is quite convenient for implantable sensors because of the low attenuation of light by skin and mammalian tissues in this spectral region and could certainly be changed by varying the particle diameter.[8B; 9B] The films also have the strong adsorption in the 500-600 nm region of the visible spectrum (FIG. 16, trace 2), which allows the utilization of light sources that are the least damaging/dangerous to skin. If necessary, both adsorption and emission of the NPs can be strongly shifted to the 800-1500 nm IR region by using dopants such as Hg (2+).[20B; 21B]

CdTe and other Cd- and Hg(2+)-containing semiconductor materials are very cytotoxic as evidenced by numerous testing reports.[22B] This prevents their direct utilization in biosensors or any other applications requiring contact with living tissue. As described above, CdTe NPs were decorated with bovine serum albumin.[23B] Besides, the remarkable optical effects observed for these bioconjugates, the albumin coating will likely substantially reduce both the toxic effect of the semiconductor and immune response of the body. Other proteins can be used as well. It should be recognized by an ordinary artisan that the choice of materials to impart biocompatibility to a biosensor of this invention containing encapsulated NPs in albumin or other coatings may interfere with the optical and electrical properties of the NP/polyelectrolyte composite. Since the most general transduction mechanism of sensor is the analyte-induced change in interparticle separation,[24B] the restrictions on the distance of the closest approach to the NP core in one preferred embodiment requires minimization of interparticle distances.

The chemical composition of the surface is the primary factor that determines the interactions with living cells. Therefore, to obviate the problem of CdTe cytotoxicity, one can coat the entire NP assembly with a suitable biological compound friendly to living cells. Following the same film preparation technique, a new series of LBL bilayers can be built on top of the CdTe film, which will form the buffer layer between the semiconductor material and tissue thereby screening the underlying CdTe NPs.

Collagen is regarded as one of the most useful biomaterials[5B; 25B] for its excellent biocompatibility. Many natural polymers and their analogues can also render surfaces suitable for implantation,[26B; 27B] but the quality of collagen as a cell adhesion promoter is difficult to surpass.[25B; 28B] Being a protein, it is also a polyelectrolyte, and thus can be easily incorporated in the LBL process. For these reasons, the NPs were combined with collagen in a stratified LBL assembly and to test the biological properties of the resulting stack.

To find the most appropriate conditions for film deposition, the collagen LBL films were initially assembled separately from NPs and then integrated with the (PDDA/CdTe)$_n$ multilayers by deposition an additional PDDA layer on top. Collagen was assembled with negatively charged PAA as a partner polyelectrolyte from aqueous solution at pH 4 when the protein is positively charged. Besides, PAA/TiO$_2$ nanoshell multilayers exhibited good biocompatibility with neuron precursor PC12 cells,[14B] which also advocated its use for CdTe coating.

The structure of (PAA/collagen)$_n$ bilayer was analyzed by AFM. In FIG. 17, one can clearly see the fibrous filaments of collagen and PAA macromolecules coating the substrate uniformly and homogeneously. Importantly, the collagen layer reveals substantial porosity with diameter of channels between 10 and 50 nm. This is sufficient for the permeation of many important biological analytes, for instance glucose, while keeping immune-response species such as macrophages at a distance. FIG. 18 shows the dependence of the ellipsometric film thickness vs. the number of LBL cycles for (PAA/collagen)$_n$ multilayers: the thickness increment initially increases and then becomes virtually constant. The average thickness per one (PAA/collagen) bilayer is 30 nm.

Biocompatibility of man-made materials is determined by the interplay of many factors, which are not completely understood. An assessment of this property cannot be done on the basis of a single physical characteristic of the interface, such as chemical composition, surface charge, roughness, or porosity, because biocompatibility is a complex interdependence thereof. Therefore, the direct test of cell attachment was used, which provides a cumulative characteristic of cell tolerance toward the material. For that, mammalian C2C12 culture cell was used that represents a convenient model for expected interactions between the prepared nanoparticle/polyelectrolyte/collagen composite and muscle tissues. When (PDDA/CdTe)$_n$ multilayer were exposed to the cell culture, virtually only clusters of dead cells were observed on the film surface as shown in FIG. 19A. When the CdTe NPs film were coated by a single PAA/collagen bilayer, the behavior of cells dramatically changes as shown in FIG. 19B. They attach in large quantities and spread over the surface indicating that the cytotoxicity of the CdTe was markedly screened. They also show the signs of aggregating in large colonies. When the number of collagen bilayers was increased to (PAA/collagen)$_5$, so did the total number of cells attached: they cover the entire surface of the sample with continuous biofilm FIG. 19C.

Conclusion

The improvement of biocompatibility of the CdTe/PDDA multilayers is the first step toward the utilization of NP/polymer composites in the biomedical field. The strong luminescence of the II-VI nanoparticles makes targeting implantable optical sensors, a logical extension of this work. The described procedure can also be used for the surface modification of sensor elements of other types of implants, as well as for production of advanced prosthetic devices and tissue engineering. While having commonality in materials requirements, such as the long-term coexistence of NP composite and living tissue, all these applications will require tailoring of the surface properties to ensure viability of different cells as well as their apposite interactions with the implant. For that reason, the universality and flexibility of LBL provides a potent approach for the materials design in the biomedical field.

Layer-by-Layer Assembly of Collagen Thin Films Controlled Thickness and Biocompatibility The preparation of ultrathin polymer films is of scientific and practical interest for various biomedical fields from tissue engineering to dialysis. Thin film biomaterials in the form of coatings or membranes can be made from either naturally occurring, synthetic polymers or a combination of both.[1D] The composite ultrathin films open the possibility of combining the biocompatibility of naturally occurring polymers with the versatility of the chemical and physical properties of synthetic polymers. Biodegradable natural polymers such as collagen are particularly attractive for such compositions.

As a fibrous protein, collagen is the major component of mammalian connective tissue.[2D] It is also involved in many important biological functions such as tissue regeneration and cell attachment.[3D,4D] Type-I collagen is the most abundant among the many types of collagen and constitutes more than 90% of all extracellular protein.[2D] In relationship to its framework-forming function in living organisms, it has the ability to self-assemble into rigid gels and fibers.[5D-7D] Thin films of type-I collagen can be easily prepared by non-specific adsorption from solution or spin-coating techniques but they display a high degree of roughness and poor strand alignment. Additionally, it is difficult to regulate film thickness, particularly when nanometer scale precision is needed, for instance, in biomineralization studies.[8D-11D] Layer-by-layer (LBL) adsorption of polyelectrolytes introduced by G. Decher in the beginning of the 1990s,[12D,13D] allows for the deposition of homogeneous, robust films with layer thickness and interlayer separation controlled on the nanometer scale. Other advantages of the assembly include the control of the surface structure, which, in turn, may be employed to govern the biological responses. A method of LBL deposition of collagen thin films is disclosed, which later can be combined with other colloids that can be LBL assembled to produce structurally and functionally versatile materials, where the importance of biomaterials made by LBL have been demonstrated.[14D-16D]

Experimental

Chemicals

All the chemicals unless otherwise specified were purchased from Sigma-Aldrich (St. Lois, Mo.) and were used without further purification. Ultrapure 18 MΩ/cm water was used for all experiments and for washing. The pH of solutions was adjusted with diluted HCl or NaOH. All experiments were performed under atmospheric conditions.

Procedures

The films with collagen layers on the different substrates (quartz, glass, silica wafer, and polystyrene cell culture plates) were constructed by LBL-assembly with a polyelectrolyte. Before the assembly, the substrates were subjected to an extensive cleaning procedure. Quartz and silica wafer were cleaned in freshly prepared "piranha" solution (2:1 concentrated $H_2SO_4$: 3% $H_2O_2$) for 5 min then rinsed extensively with water, and finally dried under a stream of nitrogen.

The LBL assembly was always started with absorption of positively charged Poly(dimethyldiallylammonium) chloride, Mw=400,000-500,000 (PDDA) on a glass, silicon or plastic substrates, which are naturally negatively charged due to partial oxidation of their surface. The sequence of operations resulting in production of collagen films was the following. The substrate was immersed in a 0.5% PDDA pH 3 for 10 min. After a 30 sec wash of the substrate in a separate beaker with deionized MΩ/cm water, the PDDA-primed substrate was dipped into a 0.5 wt % solution of poly(sodium styrenesulfonate), Mw=1,000,000 (PSS) at pH 4, which changes the surface charge to negative. Following the same washing procedure, the substrate was exposed to positively charged 0.1% solution of collagen type-I at pH 4.2 for 20 min and rinsed with water again. This procedure results in the deposition of a film with PDDA/PSS/collagen layer sequence. The further growth of PSS/collagen bilayers was accomplished by the repetition of the same cycle of immersion into the solution of PSS, rinsing, immersion into the collagen solution, and rinsing. The cycle was repeated n times to obtain a film of desirable thickness, which can be denoted as PDDA(PSS/collagen)$_n$. After the final assembly cycle, the substrate was dried with a stream of nitrogen.

For cell culture studies, the films were deposited on a bottom of a Petri dish, which served as the LBL substrate. In this case, the polyelectrolyte and collagen solutions and water for rinsing were poured into the Petri dish and remained there for the specified length of time.

Muscle myoblast cells (C2C12) and pheochromocytoma cells (PC12) were purchased from American Type Culture Collection (ATCC, Manassas, Va.). C2C12 cells were cultured in Dulbecco's Modified Eagle's medium (DMEM) containing 15% fetal bovine serum (FBS, Hyclone), 2% streptomycin/penicillin. The cells were removed from culture substrates with trypsin/EDTA 1× and centrifuged. PC12 cells were cultured in RPMI 1640 medium (GIBCO, Carlsbad, Calif.) containing 5% fetal bovine serum (FBS, Hyclone), 10% horse serum (GIBCO, Carlsbad, Calif.), and 2% streptomycin/penicillin. The PC12 cells were removed from culture substrates by pipetting with medium. Before seeding, polystyrene Petri dishes with deposited LBL layers were sterilized with ethanol. C2C12 or PC12 cells suspended in fresh medium were seeded on the substrates and allowed to adhere for 1 day in a 37° C. 5% $CO_2$/air 95% environment for 24 h (incubator, NuAir Inc., Plymouth, Minn.).

Instrumentation

Surface imaging of nanoparticles layers was performed by Nanoscope III (Digital Instruments/Veeco, Santa Barbara, Calif.). Atomic force microscopy (AFM) images were obtained in tapping mode with standard Si/N tips.

Ellipsometric measurements were made with an AutoEL MS ellipsometer from Rudolph Research Corp. (Flanders, N.J.). The measurements were performed using a 632.8 nm line of He/Ne laser incident upon the sample at 70°. The DafIBM program supplied by Rudolph Technologies was employed to determine film thickness.

UV-vis spectra were taken using a HP8453A diode array Hewlett-Packard spectrophotometer.

Zeta potentials were obtained with a Zetamaster Model 2000 (Malvern Instruments, Malvern, UK) by taking the average of (at least) three measurements at stationary level. The cell used was a 5 mm-2 mm rectangular quartz capillary. The calculation of zeta potential, $\zeta$, is realized by application of the Smoluchowski equation:

$$\zeta = \mu \eta / \epsilon,$$

where $\mu$ is electrophoretic mobility measured by the instrument, and $\eta$ and $\epsilon$ are the viscosity and permittivity of the solution, respectively.

Attached cells were imaged using a Microflex UFX-DX inverted microscope (Nikon USA, Melville, USA) with 100× and 200× magnification.

Results and Discussion

LBL Film Assembly and Structure

Figure 20B:
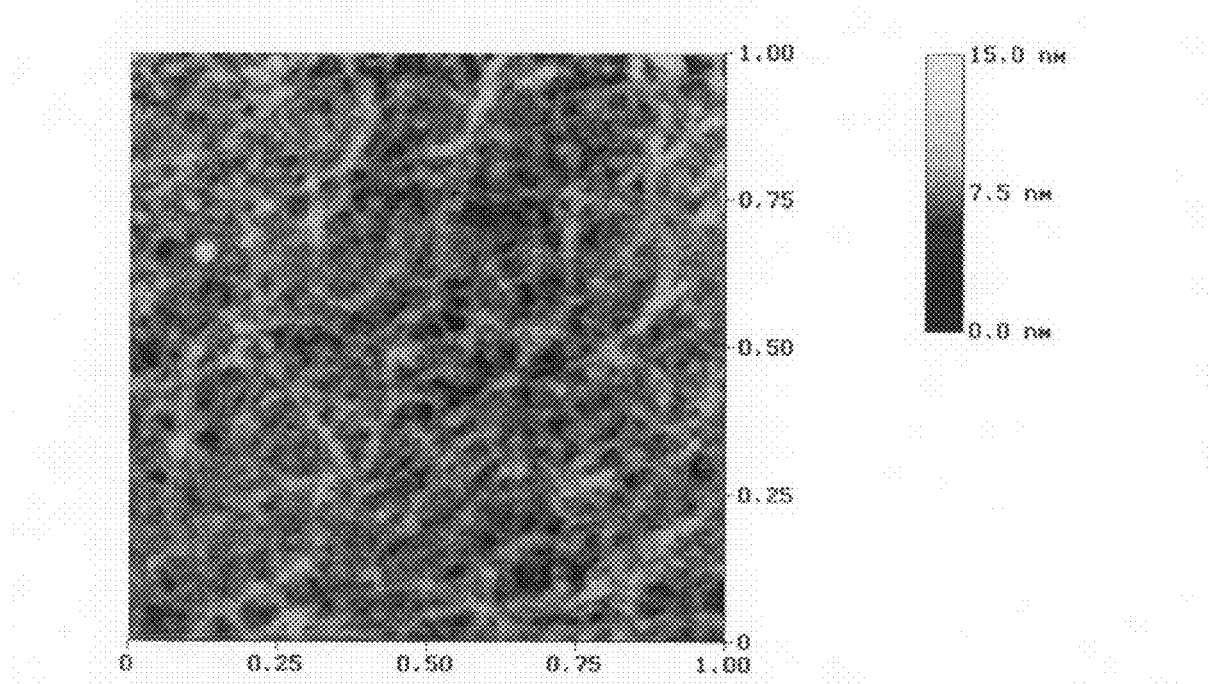

The LBL assembly procedure of collagen was performed with PSS partner polyelectrolyte. At pH 4 collagen is positively charged ($\zeta$=+7 mV), while PSS remains negatively charged ($\zeta$=55 mV) as determined by zeta-potential measurements, which enables long-distance electrostatic attraction of the polyelectrolytes to coated oppositely charged substrate. The formation of absorption layers of collagen and PSS can be seen on the AFM images as shown in FIG. 20. For the PDDA/PSS/collagen film, the morphology of the outermost layer of the protein can be described as densely interwowen protein fibers, which cover the surface uniformly and homogeneously. The dimensions of the fibers coincide well with the expected ones for this macromolecule i.e. the length of each subunit is ca. 300 nm, and the diameter of the triple helix is 1.5 nm.[2D] This type of surface topography was never observed for other polyelectrolytes or proteins including those present in serum, which typically form round aggregates 50-60 nm in average diameter.

The gradual build-up of the collagen/PSS film on quartz slides in the cyclic dipping procedure can be visualized by UV-visible spectroscopy as shown FIG. 21. The sequence of the UV spectra show a linear increase of absorbance with every new PSS/collagen bilayers, which is typical for many LBL assembled pairs. These data correlate well with the ellipsometric measurements, which also demonstrate linearity of the multilayer build-up as shown FIG. 22. Thus, it becomes possible to control the thickness of collagen film with an accuracy of 13 nm, i.e. the thickness increment corresponding to one PSS/collagen bilayer. If necessary, the layer-by-layer nature of the deposition also allows one to combine collagen layers with other LBL components to produce stratified multilayer systems of potential utility for biomedical applications.[17D-18D]

Attachment and Growth of Living Cells

The collagen surface layer of the film presents multiple adhesion sites for various types of cells. C2C12 and PC12 cells were selected for preliminary studies because these cell lines can be induced to differentiate into muscle and neuronal cells respectively. Biocompatibility of the prepared multilayers was evaluated by examining the ability of culture cells to attach to and grow on the collagen film. As shown in FIG. 23, C2C12 myoblats show clear signs of adhesion and growth on collagen/PSS multilayers with fairly uniform distribution over the entire coated area. No signs of adhesion were observed in case of exclusively polyelectrolyte PDDA/PSS coating.

One of the most important directions in biomaterials research, which requires precise control of film thickness, is neuroprosthesis. Excitation of neurons can be strongly affected by the electrode coating, and LBL appears to be a suitable technique for fine-tuning of the electrode-neuron interface. Therefore, the adhesion PC12 nerve precursor cells to the prepared collagen multilayers were tested. As evidenced by FIG. 24, the culture of PC12 pheochromocytoma cells can also attach to PDDA(PSS/collagen)$_2$ multilayers quite well. The very top layer of the assembly stack will be of primary importance determining the cell adhesion. In the same time, a non-monotonous dependence of LBL coating biocompatibility on the total number of LBL layers was reported[14] D indicating the complexity of processes determining cell/film interaction, which may also be further complicated by the slow reconstruction of thicker films.

Conclusion

Layer-by-layer assembly procedure can be used for the fabrication of PSS/collagen thin films made from interwoven protein fibers. The collagen-polyelectrolyte layers are uniform and their thickness of grows linearly with the number of deposition cycles, while the increment corresponding to one PSS/collagen bilayers prepared under specified conditions is equal to 13 nm. Such composite systems with controlled thickness of the coating and bioactive surface properties can be utilized in the fabrication of advanced biomaterials with inherent asymmetry.

REFERENCES

The following references are cited herein:
(1A) National Institute of Diabetes and Digestive and Kidney Diseases. Diabetes Overview, NIH, 94-3235, 1994.
(2A) Schultz, J. S., Mansouri, S., and Goldstein, I. J., "Affinity Sensor: A New Technique for Developing Implantable Sensors for Glucose and Other Metabolites," Diabetes Care, 5-3; pp 245-53: May-June, 1982.
(3A) Cote, G. L., "Noninvasive optical glucose sensing—an overview," Journal of Clinical Engineering, 2-4: 253-259, 1997.
(4A) Pan, S., Chung, H., Arnold, M. A. and Small, G. W., "Near-infrared spectroscopic measurement of physiological glucose levels in variable matrices of protein and triglycerides," Anal. Chem., 68, 1124-1135, 1996.
(5A) March, W. F., Rabinovitch, B., and Adams, R. L., "Noninvasive Glucose Monitoring of the Aqueous Humor of the Eye: Part 11. Animal Studies and the Scleral Lens.", Diabets Care, Vol. 5, No. 3, pp 259-65, 1982.
(6A) Wicksted, J. P., Erkens, R. J., Motamedi, M., and March, W. E., "Monitoring of aqueous humor metabolites using Raman spectroscopy," SPIE Proceedings, 2135, 264-274, 1994.
(7A) Schwartz, M., Kost, G. J., "Electrical properties of glucose-sensitive hydrogels: Swelling and conductivity relationships," Biomed. Master Res., (41): 65-70, 1998.
(8A) Shakhsher, Z., Seitz, W. R., and Legg, K. D., "Single-fiber optic pH sensor based on changes in reflection accompanying polymer swelling," Anal. Chem., 66, 1731-1736, 1994.
(9A) Russel, R. J., Gefrides, C. C., McShane, M. J., Cote, G. L., and Pishko, M. V., "A fluorescence-based glucose sensoring concababvalin A and dextran encapsulated in a poly (ethylene glycol) hydrogel," Anal. Chem., 71, 3126-3132, 1999.
(10A) Lee, S. J., Park, K., "Glucose-Sensitive Phase-Reversible Hydrogels," Am. Chem. Soc., 627, 11-16, 1994.
(11A) Bruulsema, J. T., Hayward, J. E., Farrell, T. J., Patterson, M. S., Heinemann, L., Berger, M., Koschinsky, T., Sandahl-Christansen, J., Orskov, H., Essenpries, M., Schmelzeisen-Redeker, G., Bocker, D., "Correlation between blood glucose concentration in diabetics and non-invasively measured tissue optical scattering coefficient." Optics Letters 22(3), 190-193, 1997.
(12A) D. Huang, E. A., Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science 254, 1178-1181, 1991.
(13A) Esenaliev R O, Larin K, Larina I, Motamedi M, "Non-invasive monitoring of glucose concentration with optical coherence tomography," Optics Letter (In Review).
(14A) Decher, G., Fuzzy Nanoassemblies Toward Layered Polymeric Multicomposites; Science (277) 1232-1237.
(15A) Rubner, M. F., Fabrication of Novel Molecular Assemblies of Conjugated Polymers; J. Macromol. Sci. Pure Appl. Chem. (A31): 805-809, 1994
(16A) Ariga, K.; Lvov, Y.; Ichinose, I.; Kunitake, T., Ultrathin films of inorganic materials (Si02 nanoparticle, montmorillonite microplate, and molybdenum oxide) prepared by alternate layer-by-layer assembly with organic polyions; Appl. Clay Sci., 15 1-2, 137-152, 1999.
(17A) Kotov, N. A.; Haraszti, T.; Turi, L.; Zavala, G.; Geer, R. E.; Dekany, I.; Fendler, J. H., Mechanism of and Defect Formation in the Self Assembly of Polymeric Polycation Montmorillonite Ultrathin Films; J. Amer. Chem. Soc., 119: 6821-6832, 1997.
(18A) Liu, Y. J.; Wang, Y.; Lu, H.; Claus, R. O., Electrostatic Self-Assembly of Highly-Uniform I Micrometer-Thi~k Fullerene Films; J. Phys. Chem. A. 103-12: 2035-2036, 1999.19.
(19A) Lvov, Y.; Aliga, K.; Ichinose, I.; Kunitake, T., Assembly of Multicomponent Protein Films by Means QfElectrostatic Layer by Layer Adsorption; J. Amer. Chem. Soc., 117: 6117-6123, 1995.
(20A) Sukhorukov, G. B.; Möhwald, H.; Decher, G.; Lvov, Y. M., Assembly of Polyelectrolyte Multilayer Films by Cons~cutively Alternating Adsorption of Polynucleotides and Polycations; Thin Solid Films 285: 220-223, 1996.
(21A) Elbert, D. L.; Herbert, C. B.; Hubbell, J. A., Thin Polymer Layers Formed by Polyelectrolyte Multilayer Techniques on BiQlogical Surfaces; Langmuir 15-16: 5355-5362, 1999.
(22A) Ostrander, J. W.; Mamedov, A. A.; Kotov, N. A., Switching Between Two Modes Of Linear, Layer-By-Layer Growth Of Nanoparticle-Polylectrolyte Multilayers; J. Am. Chem. Soc., JAO029578, accepted, 2000.
(23A) D. S. Koktysh, L. M. Liz-Marzan, B.-G. Yun, I. Pastoriza-Santos; R. L. Matts, Michael Giersig, C. Serra-Rodriguez, N. A. Kotov, "Layer-By-Layer Assembled Ion-Selective And Biocompatible Films Of Tioz Nanoshells For Neurochemical Monitoring," submitted to J. Am. Chem. Soc.
(24A) Mamedov, A. A.; Kotov, N. A., Free-Standing Layer-by-Layer Assembled Films of Nanoparticles; Langmuir 16-13: 5530-5533, 2000.
(1B) Decher, G. *Science* 1997, 277, 1232-1237; Kotov, N. A.; Dekany, I.; Fendler, J. H. *J. Phys. Chem.* 1995, 99, 13065-13069; Aliev, F. G.; Correa-Duarte, M. A.; Mamedov, A.; Ostrander, J. W.; Giersig, M.; Liz-Marzan, L. M.; Kotov, N. A. *Adv. Mater.* 1999, 11, 1006-1010; Ariga, K.; Lvov, Y.; Ichinose, I.; Kunitake, T. *Appl. Clay Sci.* 1999, 15, 137-152; Schrof, W.; Rozouvan, S.; Vankeuren, E.; Horn, D.; Schmitt, J.; Decher, G. *Advan. Mater.* 1998, 10, 338-341; Caruso, F.; Caruso, R. A.; Möhwald, H. *Science* 1998, 282, 1111-1114; Caruso, F.; Susha, A. S.; Giersig, M.; Möhwald, H. *Adv. Mater.* 1999, 11, 950-953; Cassagneau, T.; Fendler, J. H.; Johnson, S. A.; Mallouk, T. E. *Adv. Mater.* 2000, 12, 1363-1366; Cassagneau, T.; Mallouk, T. E.; Fendler, J. H. *J. Am. Chem. Soc.* 1998, 120, 7848-7859; Clark, S. L.; Hammond, P. T. *Adv. Mater.* 1998, 10, 1515-1519; Wang, T. C.; Chen, B.; Rubner, M. F.; Cohen, R. E. *Langmuir* 2001, 17, 6610-6615; Mattoussi, H.; Rubner, M. F.; Zhou, F.; Kumar, J.; Tripathy, S. K.; Chiang, L. Y. *Appl. Phys. Lett.* 2000, 77, 1540-1542; Clark, S. L.; Handy, E. S.; Rubner, M. F.; Hammond, P. T. *Adv. Mater.* 1999, 11, 1031-1035; Wu, A.; Yoo, D.; Lee, J. K.; Rubner, M. F. *J. Am. Chem. Soc.* 1999, 121, 4883-4891; Kovtyukhova, N. I.; Martin, B. R.; Mbindyo, J. K. N.; Mallouk, T. E.; Cabassi, M.; Mayer, T. S. *Materials Science & Engineering, C: Biomimetic and Supramolecular Systems* 2002, 19, 255-262; Kovtyukhova, N. I.; Martin, B. R.; Mbindyo, J. K. N.; Smith, P. A.; Razavi, B.; Mayer, T. S.; Mallouk, T. E. *J. Phys. Chem. B* 2001, 105, 8762-8769; Durstock, M. F.; Taylor, B.; Spry, R. J.; Chiang, L.; Reulbach, S.; Heitfeld, K.; Baur, J. W. *Synth. Met.* 2001, 116, 373-377; Luo, C.; Guldi, D. M.; Maggini, M.; Menna, E.; Mondini, S.; Kotov, N. A.; Prato, M. *Angew. Chem., Int. Ed.* 2000, 39, 3905-3909; He, J. A.; Bian, S.; Li, L.; Kumar, J.; Tripathy, S. K.;

Samuelson, L. A. *J. Phys. Chem. B* 2000, 104, 10513-10521; Bian, S.; He, J. A.; Li, L.; Kumar, J.; Tripathy, S. K. *Adv. Mater.* 2000, 12, 1202-1205; Zeng, T.; Cooper, K. L.; Claus, R. O.; Arregui, F. J. *Proc. SPIE-Int. Soc. Opt. Eng.* 2001, 4329, 445-448; Arregui, F. J.; Matias, I. R.; Liu, Y.; Lenahan, K. M.; Claus, R. O. *Opt. Lett.* 1999, 24, 596-598; Rosidian, A.; Liu, Y.; Claus, R. O. *Adv. Mater.* 1998, 10, 1087-1091; Kleinfeld, E. R.; Ferguson, G. S. *Chem. Mater.* 1995, 7, 2327-2331.

(2B) Liefeith, K. *Mater. Corros.* 2001, 52, 798-799.

(3B) Leiner, M. J. P. *Anal. Chim. Acta* 1991, 255, 209-222.

(4B) Dario, P.; De Rossi, D. *Fis. Tecnol. (Bologna)* 1988, 11, 103-125.

(5B) Wise, D. L.; Trantolo, D. J.; Atobelli, D. E.; Yaszemski, M. J.; Gresser, J. D.; Editors. *Human Biomaterials Applications;* 1996; p 462.

(6B) Mamedov, A.; Ostrander, J.; Aliev, F.; Kotov, N. A. *Langmuir* 2000, 16, 3941-3949.

(7B) Mamedov, A. A.; Kotov, N. A. *Langmuir* 2000, 16, 5530-5533.

(8B) Mamedov, A. A.; Belov, A.; Giersig, M.; Mamedova, N. N.; Kotov, N. A. *J. Am. Chem. Soc.* 2001, 123, 7738-7739.

(9B) Rogach, A. L.; Katsikas, L.; Komowski, A.; Su, D.; Eychmuller, A.; Weller, H. *Ber. Bunsen-Ges.* 1997, 101, 1668-1670.

(10B) Lvov, Y.; Antipov, A. A.; Mamedov, A.; Möhwald, H.; Sukhorukov, G. B. *Nano Lett.* 2001, 1, 125-128; Donath, E.; Sukhorukov, G. B.; Caruso, F.; Davis, S. A.; Möhwald, H. *Angew. Chem., Int. Ed.* 1998, 37, 2202-2205; Sukhorukov, G. B.; Donath, E.; Lichtenfeld, H.; Eberhard, K.; Knippel, M.; Budde, A.; Möhwald, H. *Colloids Surf, A* 1998, 137, 253-266; Jin, W.; Shi, X.; Caruso, F. *J. Am. Chem. Soc.* 2001, 123, 8121-8122; Caruso, F.; Yang, W.; Trau, D.; Renneberg, R. *Langmuir* 2000, 16, 8932-8936.

(11B) Elbert, D. L.; Herbert, C. B.; Hubbell, J. A. *Langmuir* 1999, 15, 5355-5362.

(12B) Ngankam, P. A.; Lavalle, P.; Voegel, J. C.; Szyk, L.; Decher, G.; Schaaf, P.; Cuisinier, F. J. G. *J. Am. Chem. Soc.* 2000, 122, 8998-9005.

(13B) Grant, G. G. S.; Koktysh, D. S.; Yun, B.-G.; Matts, R. L.; Kotov, N. A. *Biomedical Microdevices* 2001, 3, 301-306.

(14B) Koktysh, D. S.; Liang, X.; Yun, B.-G.; Pastoriza-Santos, I.; Matts, R. L.; Serra-Rodriguez, C.; Liz-Marzan, L.; Kotov, N. A. *Advanced Functional Materials* 2002, in press.

(15B) Picart, C.; Lavalle, P.; Hubert, P.; Cuisinier, F. J. G.; Decher, G.; Schaaf, P.; Voegel, J. C. *Langmuir* 2001, 17, 7414-7424.

(16B) Galeska, I.; Chattopadhyay, D.; Moussy, F.; Papadimitrakopoulos, F. *Biomacromolecules* 2000, 1, 202-207.

(17B) Galeska, I.; Hickey, T.; Moussy, F.; Kreutzer, D.; Papadimitrakopoulos, F. *Biomacromolecules* 2001, 2, 1249-1255.

(18B) Mendelsohn, J. D.; Barrett, C. J.; Chan, V. V.; Pal, A. J.; Mayes, A. M.; Rubner, M. F. *Langmuir* 2000, 16, 5017-5023.

(19B) Gao, M.; Lesser, C.; Kirstein, S.; Möhwald, H.; Rogach, A. L.; Weller, H. *J. Appl. Phys.* 2000, 87, 2297-2302.

(20B) Rogach, A. L.; Koktysh, D. S.; Harrison, M.; Kotov, N. A. *Chem. Mater.* 2000, 12, 1526-1528.

(21B) Harrison, M. T.; Kershaw, S. V.; Burt, M. G.; Eychmuller, A.; Weller, H.; Rogach, A. L. *Mater. Sci. Eng., B* 2000, B69-70, 355-360.

(22B) Liu, J.; Kershaw, W. C.; Liu, Y. P.; Klaassen, C. D. *Toxicology* 1992, 75, 51-62; Skowronski, T.; Jakubowski, M.; Pawlik, B. *Acta Microbiol. Pol.* 1985, 34, 309-312; Santone, K. S.; Acosta, D.; Bruckner, J. V. *J. Toxicol. Environ. Health* 1982, 10, 169-177; Kamoi, H. *Koku Eisei Gakkai Zasshi* 2001, 51, 809-821; Fischer, A. B. *Analyst (Cambridge, U.K.)* 1995, 120, 975-978.

(23B) Mamedova, N. N.; Kotov, N. A.; Rogach, A. L.; Studer, J. *Nano Lett.* 2001, 1, 281-286.

(24B) Taton, T. A.; Mirkin, C. A.; Letsinger, R. L. *Science* 2000, 289, 1757-1760.

(25B) Lee, C. H.; Singla, A.; Lee, Y. *Int. J. Pharm.* 2001, 221, 1-22.

(26B) Angelova, N.; Hunkeler, D. *Trends Biotechnol.* 1999, 17, 409-420.

(27B) Hubbell, J. A. *Bio/Technology,* 1995, 13, 565-576.

(28B) Silver, F. H.; Garg, A. K. *Drug Targeting Delivery* 1997, 7, 319-346.

(1C) Decher, G. *Science* 1997, 277, 1232-1237.

(2C) Kotov, N. A.; Dekany, I.; Fendler, J. H. *J. Phys. Chem.* 1995, 99, 13065-13069.

(3C) Correa-Duarte, M. A.; Giersig, M.; Kotov, N. A.; Liz-Marzan, L. M. *Langmuir* 1998, 14, 6430-6435.

(4C) Aliev, F.; Correa-Duarte, M.; Mamedov, A.; Ostrander, J. W.; Giersig, M.; Liz-Marzan, L.; Kotov, N. *Adv. Mater.* 1999, 11, 1006-1010.

(5C) Liu, Y. J.; Claus, R. O. *J. Amer. Chem. Soc.* 1997, 119, 5273-5274.

(6C) Rosidian, A.; Liu, Y. J.; Claus, R. O. *Advan. Mater.* 1998, 10, 1087.

(7C) Liu, Y. J.; Wang, A. B.; Claus, R. O.; *Appl. Phys. Lett.* 1997, 71, 2265-2267.

(8C) Caruso, F.; Lichtenfeld, H.; Giersig, M.; Möhwald, H. *J. Amer. Chem. Soc.* 1998, 120, 8523-8524; Donath, E.; Sukhorukov, G. B.; Caruso, F.; Davis, S. A.; Möhwald, H., *Angew. Chemie Int. Ed.* 1998, 37(16), 2202-2205; Caruso, F.; Caruso, R. A.; Möhwald, H., *Science,* 1998, 282(5391), 1111-1114.

(9C) Gao, M. Y.; Richter, B.; Kirstein, S.; Möhwald, H. *J. Phys. Chem. B* 1998, 102, 4096-4103.

(10C) Gao, M.; Zhang, Xi.; Yang, B.; Li, F.; Shen, J. *Thin Solid Films* 1996, 284-285, 242-245.

(11C) Schlenoff, J. B.; Ly, H.; Li, M. *J. Amer. Chem. Soc.* 1998, 120, 7626-7634.

(12C) Mattoussi, H.; Radzilowski, L. H.; Dabbousi, B. O.; Thomas, E. L.; Bawendi, M. G.; Rubner, M. F. *J. Appl. Phys.* 1998, 83, 7965-7974.

(13C) Cassagneau, T.; Mallouk, T. E.; Fendler, J. H. *J. Amer. Chem. Soc.* 1998, 120, 7848-7859.

(14C) Liu, Y. J.; Wang, A. B.; Claus, R. O. *Appl. Phys. Lett.* 1997, 71, 2265-2267.

(15C) Möhwald, H.; Lichtenfeld, H.; Moya, S.; Voigt, A.; Baumler, H.; Sukhorukov, G.; Caruso, F.; Donath, E.; *Macromol. Symp.,* 1999, 145, 75-81; Stroeve, P; Vasquez, V.; Coelho, M. A. N.; Rabolt, J. F. 1996, 284-285, 708-712; Levasalmi, J.-M.; McCarthy, T. J.; *Macromolecules,* 1997, 30, 1752-1757. Ackern, van F.; Krasemann, L.; Tieke, B.; *Thin Solid Films,* 327-329, 762-766.

(16C) Kotov, N. A.; Magonov, S.; Tropsha, E. *Chem. Mater.* 1998, 10, 886-895.

(17C) Kotov, N. A.; Haraszti, T.; Turi, L.; Zavala, G.; Geer, R. E.; Dekany, I.; Fendler, J. H. *J. Amer. Chem. Soc.* 1997, 119, 6821-6832.

(18C) Cassegneau, T.; Fendler, J. H. *J. Phys. Chem. B,* 1999, 103, 1789-1793

(1D) N. Angelova and D. Hunkeler. Trends Biotechnol. 17(10), 409-420 (1999).

(2D) J. M. Pachence. J. Biomed. Mater. Res. 33(1), 35-40 (1996).

(3D) J. A. Hubbell. Bio/Technology 13(6), 565-576 (1995).
(4D) J. M. Pachence, R. A. Berg, and F. H. Silver. Med. Device Diagn. Ind. 9(1), 49-55 (1987).
(5D) D. L. Christiansen, E. K. Huang, and F. H. Silver. Matrix Biol. 19(5), 409-420 (2000).
(6D) G. D. Pins and F. H. Silver. Mater. Sci. Eng., C C3(2), 101-107 (1995).
(7D) F. H. Silver and A. K. Garg. Drug Targeting Delivery 7 (Handbook of Biodegradable Polymers), 319-346 (1997).
(8D) D. A. Carrino, J. E. Dennis, T. M. Wu, J. L. Arias, M. S. Fernandez, J. P. Rodriguez, D. J. Fink, A. H. Heuer, and A. I. Caplan. Connect. Tissue Res. 35(1-4), 325-329 (1996).
(9D) G. Falini, S. Fermani, M. Gazzano, and A. Ripamonti. Chem.—Eur. J. 4(6), 1048-1052 (1998).
(10D) O. Nakamura and A. I. Caplan. J. Bone Miner. Metab. 12(1), 17-25 (1994).
(11D) T. Uemura, Y. K. Liu, Y. Feng, A. Nemoto, T. Yabe, T. Ushida, H. Miyamoto, and T. Tateishi. Mater. Sci. Eng., C C4(4), 303-309 (1997).
(12D) G. Decher. Science 277, 1232-1237 (1997).
(13D) G. Decher and J. D. Hong. Macromol. Chem., Macromol. Symp. 46, 321 (1991).
(14D) D. L. Elbert, C. B. Herbert, and J. A. Hubbell. Langmuir 15(16), 5355-5362 (1999).
(15D) D. S. Koktysh, N. A. Kotov, I. Pastoriza-Santos, L. M. Liz-Marzan, B.-G. Yun, and R. L. Matts, in preparation (2001).
(16D) P. A. Ngankam, P. Lavalle, J. C. Voegel, L. Szyk, G. Decher, P. Schaaf, and F. J. G. Cuisinier. J. Am. Chem. Soc. 122(37), 8998-9005 (2000).
(17D) F. Aliev, M. Correa-Duarte, A. Mamedov, J. W. Ostrander, M. Giersig, L. Liz-Marzan, and N. Kotov. Adv. Mater. 11(12), 1006-1010 (1999).
(18D) A. Mamedov, J. Ostrander, F. Aliev, and N. A. Kotov. Langmuir 16(8), 3941-3949 (2000).

All references cited herein are incorporated herein by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A biosensor/detector apparatus comprising:
   an external excitation electronic component adapted to generate an input waveform,
   a biosensor membrane component comprising:
      a multiple layered film including:
         at least two layer-by-layer assembled (LBL) layers, each LBL layer including at least one positively charged layer and at least one negatively charged layer, where the layers alternate between a positively charged layer and a negatively charged layer,
         at least one responsive layer interposed between the two LBL layers, where the responsive layer has a detectable property that undergoes a change due to a change in a concentration of a target agent associated with a biological system,
         at least one of the negatively charged layers includes a detection enhancing component comprising nano-particles, where the detection enhancing component improves detection of the detectable property of the at least one responsive layer, and
         at least one bio-compatible layer deposited on each LBL layer, where the bio-compatible layer reduces cytotoxicity of the detection enhancing components,
      where the membrane component is adapted to be placed in contact with or implanted into a living biological system and where the member interacts with the input waveform to produce an output waveform,
   an external detection electronic component adapted to receive the output waveform and to generate a response signal corresponding to the output waveform, where the response signal corresponds to a value of the detectable property of the at least one responsive layer, and an external analyzer adapted to convert the response signal into a corresponding value of the detectable property, which corresponds to a concentration of the target agent associated with the living biological system.

2. The apparatus of claim 1, wherein the film further includes a plurality of responsive layers, where the responsive layers are the same or different.

3. The apparatus of claim 1, wherein the film further includes a plurality of responsive layers interposed between LBL layers, where the responsive layers are the same or different.

4. The apparatus of claim 1, wherein the membrane component further comprises a mesh surrounding the film.

5. The apparatus of claim 4, wherein the membrane component further comprises a coating surrounding the mesh.

6. The apparatus of claim 1, wherein the responsive layers forms a pattern, where the pattern comprises vertical strips, horizontal strips or patches.

7. The apparatus of claim 1, wherein the detectable property is a physical dimension, which changes in response to the change in the concentration of the target agent or responsive layer includes a marker that undergoes a change in response to the change in the concentration of the target agent, where the marker includes a dye, a fluorescent dye, a fluorescent donor-acceptor pair, a dye capable of undergoing FRET, or mixtures and combinations thereof.

8. The apparatus of claim 1, wherein the target agent comprises an atom, ion, molecule and/or molecular assembly.

9. The apparatus of claim 1, wherein the target agent comprises glucose and the detectable property is a physical dimension, which changes in response to the change in the concentration of the target agent.

10. The apparatus of claim 1, wherein the detection electronic component comprises an electromagnetic detection system, an acoustic detection system, or a spectroscopic detection system.

11. The apparatus of claim 1, wherein the living biological system comprises a tissue, an organ, a cell culture, a tissue culture, or a mixture or combination thereof.

12. The apparatus of claim 1, wherein the positively charged organic polymer comprises poly(diallyldimethylammonium) polycation (PDDA) or collagen.

13. The apparatus of claim 1, wherein the membrane component further comprises end caps coated on, pressed on or applied to ends of the membrane component.

14. The apparatus of claim 1, wherein the nano-particles comprise semiconductor nano-particles and the bio-compatible layer comprises collagen.

15. The apparatus of claim 14, wherein the semiconductor nano-particles comprise CdTe nano-particles.

16. A biosensor/detector apparatus comprising:
   a membrane comprising:
      an excitation electronic component adapted to generate an input waveform, a biosensor component comprising:
- at least two layer-by-layer assembled (LBL) layers, each LBL layer including at least one positively charged layer and at least one negatively charged layer, where the layers alternate between a positively charged layer and a negatively charged layer,
- at least one responsive layer interposed between the two LBL layers, where the responsive layer has a detectable property that undergoes a change due to a change in a concentration of a target agent associated with a biological system,
- at least one of the negatively charged layers includes a detection enhancing component comprising nano-particles, where the detection enhancing component improves detection of the detectable property of the at least one responsive layer, and
- at least one bio-compatible layer deposited on each LBL layer, where the bio-compatible layer reduces cytotoxicity of the detection enhancing components, where the biosensor component interacts with the input waveform to produce an output waveform, and
a detection electronic component adapted to receive the output waveform and to generate a response signal corresponding to the output waveform, where the response signal corresponds to a value of the detectable property of the at least one responsive layer and where the detection electronic component includes a transmitter for transmitting the response signal,
where the components are collinearly disposed with the biosensor component interposed between the excitation electronic component and the detection electronic component and where the membrane is adapted to be placed in contact with or implanted into a living biological system, and
an external analyzer adapted to convert the response signal into a corresponding value of the detectable property, which corresponds to a concentration of the target agent associated with the living biological system.

17. The apparatus of claim 16, wherein the biosensor further includes a plurality of responsive layers, where the responsive layers are the same or different.

18. The apparatus of claim 16, wherein the biosensor further includes a plurality of responsive layers interposed between LBL layers, where the responsive layers are the same or different.

19. The apparatus of claim 16, wherein the membrane further comprises a mesh surrounding the membrane.

20. The apparatus of claim 19, wherein the membrane further comprises a coating surrounding the mesh.

21. The apparatus of claim 16, wherein the responsive layers forms a pattern, where the pattern comprises vertical strips, horizontal strips or patches.

22. The apparatus of claim 16, wherein the living biological system is a tissue, an organ, a cell culture, a tissue culture, or a mixture or combination thereof.

23. The apparatus of claim 16, wherein the electronic components are field activated components.

24. The apparatus of claim 16, wherein the detectable property is a physical, a chemical, a biochemical, and/or a molecular property and where the target agent comprises an atom, an ion, a molecule and/or a molecular assembly.

25. The apparatus of claim 16, wherein the detectable property is a physical dimension, which changes in response to the change in the concentration of the target agent or responsive layer includes a marker that undergoes a change in response to the change in the concentration of the target agent, where the marker includes a dye, a fluorescent dye, a fluorescent donor-acceptor pair, a dye capable of undergoing FRET, or mixtures and combinations thereof.

26. The apparatus of claim 16, wherein the target agent comprises an atom, ion, molecule and molecular assembly.

27. The apparatus of claim 16, wherein the target agent comprises glucose and the detectable property is a physical dimension, which changes in response to the change in the concentration of the target agent.

28. The apparatus of claim 16, wherein the positively charged organic polymer comprises poly(diallyldimethylammonium) polycation (PDDA) or collagen.

29. The apparatus of claim 16, wherein the membrane further comprises end caps coated on, pressed on or applied to ends of the membrane.

30. The apparatus of claim 16, wherein the nano-particles comprise semiconductor nano-particles and the bio-compatible layer comprises collagen.

31. The apparatus of claim 30, wherein the semiconductor nano-particles comprise CdTe nano-particles.

32. A biosensor/detector apparatus comprising:
a membrane comprising:
an excitation electronic component adapted to generate an input waveform,
a biosensor component comprising:
- at least two layer-by-layer assembled (LBL) layers, each LBL layer including at least one positively charged layer and at least one negatively charged layer, where the layers alternate between a positively charged layer and a negatively charged layer,
- at least one responsive layer interposed between the two LBL layers, where the responsive layer has a detectable property that undergoes a change due to a change in a concentration of a target agent associated with a biological system,
- at least one of the negatively charged layers includes a detection enhancing component comprising nano-particles, where the detection enhancing component improves detection of the detectable property of the at least one responsive layer,
- at least one bio-compatible layer deposited on each LBL layer, where the bio-compatible layer reduces cytotoxicity of the detection enhancing components, and
- a mesh surrounding the biosensor, where the biosensor component interacts with the input waveform to produce an output waveform, and
a detection electronic component adapted to receive the output waveform and to generate a response signal corresponding to the output waveform, where the response signal corresponds to a value of the detectable property of the at least one responsive layer and where the detection electronic component includes a transmitter for transmitting the response signal,
where the components are collinearly disposed with the biosensor component interposed between the excitation electronic component and the detection electronic component and where the membrane is adapted to be placed in contact with or implanted into a living biological system, and
an external analyzer adapted to convert the response signal into a corresponding value of the detectable property, which corresponds to a concentration of the target agent associated with the living biological system.

33. The apparatus of claim 32, wherein the membrane further comprises a coating surrounding the mesh.

34. The apparatus of claim 32, wherein the biosensor further includes a plurality of responsive layers, where the responsive layers are the same or different.

35. The apparatus of claim 32, wherein the biosensor further includes a plurality of responsive layers interposed between LBL layers, where the responsive layers are the same or different.

36. The apparatus of claim 32, wherein the responsive layers forms a pattern, where the pattern comprises vertical strips, horizontal strips or patches.

37. The apparatus of claim 32, wherein the living biological system is a tissue, an organ, a cell culture, a tissue culture, or a mixture or combination thereof.

38. The apparatus of claim 32, wherein the electronic components are field activated components.

39. The apparatus of claim 32, wherein the detectable property is a physical, a chemical, a biochemical, and/or a molecular property and where the target agent comprises an atom, an ion, a molecule and/or a molecular assembly.

40. The apparatus of claim 32, wherein the detectable property is a physical dimension, which changes in response to the change in the concentration of the target agent or responsive layer includes a marker that undergoes a change in response to the change in the concentration of the target agent, where the marker includes a dye, a fluorescent dye, a fluorescent donor-acceptor pair, a dye capable of undergoing FRET, or mixtures and combinations thereof.

41. The apparatus of claim 32, wherein the target agent comprises an atom, ion, molecule and molecular assembly.

42. The apparatus of claim 32, wherein the target agent comprises glucose and the detectable property is a physical dimension, which changes in response to the change in the concentration of the target agent.

43. The apparatus of claim 32, wherein the positively charged organic polymer comprises poly(diallyldimethylammonium) polycation (PDDA) or collagen.

44. The apparatus of claim 32, wherein the membrane further comprises end caps coated on, pressed on or applied to ends of the membrane.

45. The apparatus of claim 32, wherein the nano-particles comprise semiconductor nano-particles and the bio-compatible layer comprises collagen.

46. The apparatus of claim 45, wherein the semiconductor nano-particles comprise CdTe nano-particles.

* * * * *